(12) United States Patent
Biris et al.

(10) Patent No.: US 9,198,934 B2
(45) Date of Patent: Dec. 1, 2015

(54) COMPOSITIONS COMPRISING NANOPARTICLES AND APOPTOTIC AGENTS AND METHODS OF USE

(75) Inventors: Alexandru S. Biris, Little Rock, AR (US); Meena Mahmood, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 46 days.

(21) Appl. No.: 12/775,210

(22) Filed: May 6, 2010

(65) Prior Publication Data

US 2010/0285138 A1 Nov. 11, 2010

Related U.S. Application Data

(60) Provisional application No. 61/215,494, filed on May 6, 2009.

(51) Int. Cl.
| | |
|---|---|
| *A61K 9/14* | (2006.01) |
| *A61K 33/24* | (2006.01) |
| *A61K 31/573* | (2006.01) |
| *A61K 31/7048* | (2006.01) |
| *A61K 33/38* | (2006.01) |
| *A61K 45/06* | (2006.01) |
| *A61K 9/51* | (2006.01) |

(52) U.S. Cl.
CPC .................. *A61K 33/24* (2013.01); *A61K 9/143* (2013.01); *A61K 9/145* (2013.01); *A61K 31/573* (2013.01); *A61K 31/7048* (2013.01); *A61K 33/38* (2013.01); *A61K 45/06* (2013.01); *A61K 9/51* (2013.01)

(58) Field of Classification Search
CPC ......... A61K 9/51; A61K 9/143; A61K 9/145; A61K 31/573; A61K 31/7048; A61K 33/24; A61K 33/38; A61K 45/06; A61K 2300/00
See application file for complete search history.

(56) References Cited

U.S. PATENT DOCUMENTS

2006/0173362 A1* 8/2006 Toms et al. .................... 600/478
2008/0045865 A1* 2/2008 Kislev .............................. 601/3

OTHER PUBLICATIONS

Rothen-Rutishauser BM, Schurch S, Haenni B, Kapp N, Gehr P. 2006. Interaction of fine particles and nanoparticles with red blood cells visualized with advanced microscopic techniques. Environ. Sci. Technol. 40:4353-4359.
Sayes CM, Liang F, Hudson JL, Mendez J, Guo W, Beach JM, Moore VC, Doyle CD, West JL, Billups WE, Ausmanb KD, Colvin VL. 2006. Functionalization density dependence of single-walled carbon nanotubes cytotoxicity in vitro. Toxicol. Lett. 161: 135-142.
Tewari M, Quan LT, O'Rourke K, Desnoyers S, Zeng Z, Beidler DR, Poirier GG, Salvesen GS, Dixit VM. 1995. Yama/CPP32 beta, a mammalian homolog of CED-3, is a CrmA-inhibitable protease that cleaves the death substrate poly (ADP-ribose) polymerase. Cell 81: 801-809.
Wen LT, Caldwell CC, Knowles AF. 2003. Poly(ADP-ribose) polymerase activation and changes in Bax protein expression associated with extracellular ATP-mediated apoptosis in human embryonic kidney 293-P2X7 cells. Mol. Pharmacol. 63: 706-713.
Xia T, Kovochich M, Brant J, Hotze M, Sempf J, Oberley T, Sioutas C, Yeh JI, Wiesner MR, Nel AE. 2006. Comparison of the abilities of ambient, and manufactured nanoparticles to induce cellular toxicity according to an oxidative stress paradigm. Nanoletters 6: 1794-1807.
Zanello LP, Zhao B, Hu H, Haddon RC. 2006. Bone cell proliferation on carbon nanotubes. Nanoletters 6: 562-567.
Zharov V, Galitovsky V, Viegas M. 2003. Photothermal detection of local thermal effects during selective nanophotothermolysis. Appl. Phys. Lett. 83: 4897-4899.
Zharov VP, Galitovskaya EN, Jonson C, Kelly T. 2005. Synergistic enhancement of selective nanophotothermolysis with gold nanoclusters: potential for cancer therapy. Laser Surg. Med. 37: 219-226.
Meena Mahmood, Daniel A. Casciano, Teodor Mocan. 2009 John Wiley & Sons Ltd., Published online in Wiley InterScience Sep. 16, 2009. Cytotoxicity and Biological Effects of functional Nanomaterials Delivered to Various Cell Lines. J. Appl. Toxicol. 2010; 30: 74-83.
Z. Liu, K. Chen, C. Davis, S. Sherlock, Q. Cao, X. Chen, H. Dai, Cancer Res. 2008, 68, 6652.
M. Prato, K. Kostarelos, a. Bianco, Acc. Chem. Res. 2008, 41, 60.
S. Hampel, D. Kunze, D. Haase, K. Krämer, M. Rauschenbach, M. Ritschel, A. Leonhardt, J. Thomas, S. Oswald, V. Hoffmann, B. Büchner, Nanomed, 2008, 3, 175.
P. Arimondo, C. Boukarim, C. Bailly, D. Dauzonne, C. Monneret Anti-Cancer Drug Design, 2000,15, 413.
A. Paola, B. Chawki, B. Christian, D. Daniel, M. Claude, Anti-cancer drug design, 2000, 15, 413.
J.S. Kim, G.P. Amorino, H. Pyo, Q. Cao, H. Choy, Radiother. Oncol. 2002, 62, 61.
K. D. Bromberg, A. B. Burgin, and N. Osheroff., J. Biol. Chem., 2003, 278, 7406.
B.A. Teicher, Clin Cancer Res, 2008, 14, 1610.
E. Thomas E, P. Dumas, J.A. Ajani, Invest New Drugs. 1999, 16, 333.
S. M. Herbert, M. J. Brames, L. H. Einhorn. Journal of Clinical Oncology, 2006, 24, 18618.

(Continued)

*Primary Examiner* — Johann R Richter
*Assistant Examiner* — David Browe
(74) *Attorney, Agent, or Firm* — Tim Tingkang Xia, Esq.; Locke Lord LLP

(57) ABSTRACT

Compositions comprising nanoparticles, such as silver or gold nanoparticles or carbon nanotubes (CNTs), and apoptotic agents are described. The nanoparticles can significantly enhance the cancer chemotherapeutic effects of the apoptotic agents. In particular, a highly increased anti-tumor activity has been demonstrated for the combination of etoposide and CNTs against HeLa cells compared to the administration of either etoposide alone or nanoparticles alone. Data provided by flow cytometry, Caspase 3 and other methods, suggest a strong interaction between the nanoparticles and the cellular structure, which can result in the improved effectiveness of chemotherapeutic agents. These findings provide potential new cancer therapies by carefully selecting the right combination of cytostatic drugs and nanostructural materials which synergistically provide significantly greater curative rates.

10 Claims, 25 Drawing Sheets

(56) References Cited

OTHER PUBLICATIONS

N. Hijiya, A. Gajjar, Z. Zhang, J.T. Sandlund, R.C. Ribeiro, J.E. Rubnitz, S. Jeha, W. Liu, C. Cheng, S.C. Raimondi, F. G. Behm, G.K. Rivera, M.V. Relling, and C.H. Pui, Leukemia, 2004, 18, 1581.

C.L. Perkins, F. Guofu, K.N. Caryn, K. N. Bhalla., Cancer Research, 2000, 60, 1645.

C. Stefanellia, B. Tantinia, M. Fattoria, I. Stanic'a, C. Pignattia, C. Clob, C. Guarnieri, C. M. Caldareraa, C. A. Mackintoshc, A. E. Peggc, F. Flamignia, FEBS Letters 2002, 527, 223.

D. J. Smart, H. D. Halicka, G. Schmuck, F. Traganos, Z. Darzynkiewicz, and G. M. Williams, Mutat Res. 2008, 641, 43.

P. Koistinen, T. Siitonen, P. Mäntymaa, E. Savolainen, Leukemia Research, 2001, 25, 1099.

A. S. Moosavi, A. Tehranian, N. Behtash, M. Modares Gilani and F. Ghaemmaghami, Acta Medica Iranica, 2006, 44,7.

G. Spitaleri, D. V. Matei, G. Curigliano1, S. Detti, F. Verweij, S. Zambito, E. Scardino, B. Rocco, F. Nole, L. Ariu, T. De Pas, F. de Braud, O. D. Cobelli, Annals of Oncology, 2009, doi:10.1093/annonc/mdn650.

M.J. Boyer, P. Mitchell, D. Goldstein, M.J. Millward, I.N. Olver, S.J. Clarke, G. Richardson, I. Davis , Lung Cancer, 2001, 32, 89.

T. Morisaki, M.Katano, Curr. Med Chem. 2003, 10, 2517.

J. Li, M. Srinivasula, L. Feng-Ting, A. C. Newland, T. Fernandes-Alnemri, E. S. Alnemri, S. M. Kelsey, Blood, 2001, 98, 414.

H. Mirzaie-Joniani, D. Eriksson, A. Sheikholvaezin, A. Johansson, P.O. Löfroth, L. Johansson, T. Stigbrand, Cancer, 2002, 94, 1210.

P. Seminara, C. Pastore, C. Iascone, F. Cicconetti, G. Nigita, T. Ielapi, F. Franchi, Chemotherapy, 2007, 53, 218.

R.K. Reddy, C. Mao, P. Baumeister, R.C. Austin, R.J. Kaufman, A.S. Lee, Biol. Chem., 2003, 278, 20915.

T. Panaretakis, K. Pokrovskaja, M. C. Shoshan, and D. Grandér, J. Biol. Chem., 2002, 277, 44317.

L. T. Wen, C. C. Caldwell, and A. F. Knowles, Cells, 2003, 63, 706.

J.M. Van Maanen, J. Retèl, J. de Vries, H. M.Pinedo, J Natl Cancer Inst., 1988, 80, 1526.

J.H Hwang, J.Y. Kim, M.I. Cha, I.N. Ryoo, S.J. Choo, S.M. Cho, Y. Tsukomu, A. Tomida, K. Shin, Y.I. Hwang, I. D. Yoo, H. R. Park. J. Cell. Physiol., 2008, 215, 243.

M.S. Soengas, P. Capodieci, D. Polsky, Nature, 2001, 409, 207.

G.S. Wu, Z. Ding, Oncogene, 2002, 21,1.

T. L. Rothstein, Cell Research, 2000, 10, 245.

S.K. Manna, S. Sarkar, J. Barr, K. Wise, E.V. Barrera, O. Jejelowo, A.C. Rice-Ficht, G.T. Ramesh, Nano Lett., 2005, 5,1676.

N.W. Shi Kam, T.C. Jessop, P.A. Wender, H. Dai, J Am Chem Soc., 2004, 126, 6850.

N. Andre, X. Tian, M. Lutz, L. Ning, Science, 2006, 311, 622.

E. Shashkov, M. Everts, E. Galanzha, V. Zharov, Nano Lett., 2008, 8, 3953.

Alnemri ES, Livingston DJ, Nicholson DW, Salvesen G, Thornberry NA,Wong WW, Yuan J. 1996. Human ICE/CED-3 protease nomenclature.Cell 87: 171.

Borm PJ, Robbins D, Haubold S, Kuhlbusch T, Fissan H, Donaldson K, Schins R, Stone V, Kreyling W, Lademann J. 2006. The potential risk of nanomaterials: a review carried out for ECETOC. Part. Fibre Toxicol. 3:11-46.

Boulares AH, Yakovlev AG, Ivanova V, Stoica BA, Wang G, Iyer S, Smulson M. 1999. Role of poly (ADP-ribose) polymerase (PARP) cleavage in apoptosis. J. Biol Chem. 274: 22932-22940.

Cryns V, Yuan J. 1998. Proteases to die for. Genes Dev. 12: 1551-1570.

Dong W, Zhang T, Epstein J, Cooney L, Wang H, Li Y, Jiang Y, Cogbill A, Varadan V, Tian RZ. 2007. Multifunctional nanowire bioscaffolds on titanium. Chem. Mater. 19: 4454-4459.

Geiser M, Rothen-Rutishauser B, Kapp N, Schurch S, Kreyling W, Schulz H, Semmler M, ImHof V, Heyder J, Gehr P. 2005. Ultrafine particles cross cellular membranes by nonphagocytic mechanisms in lungs and in cultured cells. Environ. Health Perspect. 113: 1555-1560.

Harrison BS, Atala A. 2007. Carbon nanotube applications for tissue engineering. Biomaterials 28: 344-353.

Hirsch LR, Staff ord RJ, Bankson JA, Sershen SR, Rivera B, Price RE, Hazle JD, Halas NJ, West JL. 2003. Nanoshell-mediated near-infrared thermal therapy of tumors under magnetic resonance guidance. Proc. Natl Acad. Sci. USA 100: 13549-13554.

Joe EK, Wei X, Anderson RR, Lin CP. 2003. Selective cell targeting with light-absorbing microparticles and nanoparticles. Biophys. J. 84: 4023-4032.

Kam NWS, O'Connell M, Wisdom JA, Dai H. 2005. Carbon nanotubes as multifunctional biological transporters and near-infrared agents for selective cancer cell destruction. Proc. Natl Acad. Sci. 102: 11600-11605.

Kang S, Herzberg M, Rodrigues DF, Elimelech M. 2008. Antibacterial effects of carbon nanotubes: size does matter! Langmuir 24: 6409-6413.

Liu Z, Davis C, Cai W, He L, Chen X, Dai H. 2008. Circulation and long-term fate of functionalized, biocompatible single-walled carbon nanotubes in mice probed by Raman spectroscopy. Proc. Natl Acad. Sci. 105: 1410-1415.

National Research Council. 2007. Toxicity Testing in the 21st Century: a Vision and a Strategy. National Academic Press: Washington, DC.

Nicholson DW, Ali A, Thornberry NA, Vaillancourt JP, Ding CK, Gallant M, Gareau Y, Griffi n PR, Labelle M, Lazebnik YA, Munday NA, Raju SM, Smulson ME, Yamin TT, Yu VL, Miller DK. 1995. Identification and inhibition of the ICE/CED-3 protease necessary for mammalian apoptosis. Nature 376: 37-43.

Oberdorster G, Oberdorster E, Oberdorster J. 2005b. Nanotoxicology: An emerging discipline evolving from studies of ultrafine particles. Environ. Health Perspect. 133: 823-839.

Panyam J, Labhasetwar V. 2003. Biodegradable nanoparticles for drug and gene delivery to cells and tissue. Adv. Drug Del. Rev. 55: 329-347.

* cited by examiner

COMPOSITIONS COMPRISING NANOPARTICLES AND APOPTOTIC AGENTS AND METHODS OF USE

This application claims the benefit of Provisional U.S. Patent Application Ser. No. 61/215,494, filed on May 6, 2009, which is incorporated by reference herein in its entirety.

The section headings used herein are for organizational purposes only and should not be construed as limiting the subject matter described herein in any way.

BACKGROUND

1. Field

This application relates to compositions comprising carbon nanotubes and anti-tumor drugs and to method of using these compositions.

2. Background of the Technology

In addition to precise targeting tumor and toxicity concerns, drug resistance remains a major obstacle for the treatment of advanced cancerous tumors. Etoposide is one of the most widely used chemotherapeutic drugs. Etoposide is a derivative of podophyllotoxin with apoptotic action due to its ability to inhibit the topoisomerase II enzyme.

Etoposide is commonly used in the treatment of different malignant neoplasms such as Ewing's sarcoma, leukemia, and tumors of the brain, lung, testis, stomach and pancreas. Despite advances in treatment protocols, etoposide still has a modest response rate which varies from 1-5% in pancreatic cancer, 4% in breast cancer, 6% in ovarian cancer, 8% in cervical cancer, 19% in gastric cancer, and up to 45% in small cell lung cancer. There is an active worldwide ongoing research aiming to block the resistance response of malign cells to etoposide and other chemotherapeutic agents.

During the past decade there has been a rapid growth of research in the areas of nanomaterials and nanoscience because of the realization that these small size materials can be used in a multitude of industrial and biomedical processes. Some of the most promising applications include structural engineering, electronics, optics, consumer products, alternative energy, soil and water remediation, or for medicinal uses as therapeutic, diagnostic or drug delivery devices [49]. The promising field of nanomedicine offers the potential of monitoring, repairing, constructing and controlling human biological systems at the molecular level [49, 36] and has resulted in the engagement by drug companies in a wide array of nanotechnology research. Despite these potential benefits to society, there is concern that exposure of humans to certain types of nanomaterials may lead to significant adverse health outcomes. Among these nanomaterials, specific concern is expressed about the possible toxicity of nanoparticles (NP), which may be defined as materials with a diameter below 100 nm, and nanotubes (NT) which have two dimensions below 100 nm but the third (axial) dimension can be much larger [36]. The scientific community is responding to these concerns by consideration of the challenges to understanding exposure pathways and toxicokinetics and applying current toxicology testing methodologies, including in vitro and in vivo systems, previously used to understand the toxicology of air pollutant particles, metal fumes, radionuclides, nuisance dust, silica, asbestos and synthetic fibers [49]. However, it is also recognized that, because of the development of new methodologies derived from emerging technologies like DNA microarray, proteomics and metabolomics, new thinking is required not only in understanding toxicology associated with nanomaterials, but in the understanding of all toxicants to which the human is exposed [47]. Because of the unique dimensional and morphological properties of nanomaterials, a large number of applications have been developed that hold significant promise in the successful targeting of cancer [43, 58], tumor ablation [57, 42], drug and gene delivery [50] and especially tissue engineering [41]. Additionally, a large number of research publications have indicated that nanomaterials have the ability to interact very strongly with a variety of biological systems. For example, it was shown that titanium dioxide ($TiO_2$) nano-morphologically modified coatings can be used to reduce the adverse inflammatory effects of titanium implants and promote more advanced tissue healing following surgical procedures [39]. Also, a number of cell lines of different origins have been shown to grow on nanobased substrates, such as carbon nanotubes or other nanomaterials, indicating their potential use to evaluate the efficacy of nano-products as well as potential toxicity of nanomaterials [56]. Moreover its been amply demonstrated that there is a reasonably rapid uptake of nanomaterials into cells resulting in the interaction of these nanomaterials with various subcellular components and organelles indicating their potential for delivery to different cellular compartments [44, 55]. Therefore, a more thorough understanding of the potential cytotoxic effects of such nanomaterials is required.

Accordingly, there still exists a need for improved compositions and methods for treating cancer.

SUMMARY

A composition is provided which comprises:
nanoparticles; and
an apoptotic agent.

According to some embodiments of the composition, the apoptotic agent is etoposide. According to some embodiments of the composition, the nanoparticles are not surface modified and the apoptotic agent is not conjugated (e.g., not covalently conjugated) to the nanoparticles.

A method is also provided which comprises contacting malignant cells with nanoparticles and an apoptotic agent.

A pharmaceutical composition is also provided which comprises:
nanoparticles;
an apoptotic agent; and
a pharmaceutically acceptable carrier or excipient.

According to some embodiments of the pharmaceutical composition, the apoptotic agent is etoposide. According to some embodiments of the pharmaceutical composition, the nanoparticles are not surface modified and the apoptotic agent is not conjugated (e.g., covalently conjugated) to the nanoparticles.

A method for the treatment of cancer is also provided which comprises administering to an individual in need thereof a composition comprising nanoparticles and an apoptotic agent.

According to some embodiments of the method, the apoptotic agent is etoposide. According to some embodiments of the method, the nanoparticles are not surface modified and the apoptotic agent is not conjugated (e.g., covalently conjugated) to the nanoparticles.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

FIGS. 2A-2C are optical images of a single HeLa cell morphology before (FIG. 2A) and after (FIG. 2B) the delivery of CNTs alone (5 µg/ml, 24 hours incubation time) wherein FIG. 2C is an image of a HeLa cell that was exposed for 24 hours to CNT (5 µg/ml) and an additional 6 hours to etoposide ($75 \times 10^{-6}$M) and wherein it can be seen that as the cells die, the nanotubes were found to aggregate inside the various cellular subcompartments.

FIG. 4 are images illustrating Caspase3 activity in HeLa cell cultures wherein

FIG. 8 illustrates the relationship between the osteocytic bone cell size and the type of nanomaterials wherein the cells were cultured at a density of $10^5/35$ mm dish and incubated with ($0.5 \times 10^{-9}$ M) of Au-NPs, Ag-NPs and SW-CNTs, wherein the results obtained from four consecutive experiments are presented, wherein the magnification was 40× and the scale was 50 µm and wherein

FIGS. 10A-10D are microscopic images showing apoptosis in osteocytic bone cells wherein the images show the cellular changes due to the delivery of Ag nanoparticles and apoptotic agent (E) and wherein FIG. 10A shows cells were cultured with silver nanoparticles overnight and treated with higher concentration (0.5×10−9 M) of the apoptotic agent (E), FIG. 10B shows nuclear chromatin condensation and cellular membrane blabbing, FIG. 10C shows cellular shrinkage and FIG. 10D shows cellular lysis and disintegration by the comparison with live cells.

FIGS. 11A-11K are images showing the detection of Hela apoptotic cells using active caspase-3 staining kit wherein the cells were observed under fluorescent microscope and caspase positive cells appear to have a brighter signal whereas caspase-negative control cells show much weaker signals and wherein FIG. 11A shows Hela cells cultured with the appropriate growth medium as a control, FIG. 11B shows cells cultured with a vehicle (ethanol and DMSO), FIG. 11C shows cells cultured with gold nanoparticles, FIG. 11D shows cells cultured with gold nanoparticles and dexamethasone, FIG. 11E shows cells cultured with gold nanoparticles and etoposide, FIG. 11F shows cells cultured with silver nanoparticles, FIG. 11G shows cells cultured with silver nanoparticles and dexamethasone, FIG. 11H shows cells cultured with silver nanoparticles with etoposide, FIG. 11I shows cells cultured with single-wall carbon nanotubes, FIG. 11J shows cells cultured with single-wall carbon nanotubes and dexamethasone and FIG. 11K shows cells cultured with single-wall carbon nanotubes and etoposide.

DESCRIPTION OF THE VARIOUS EMBODIMENTS

Figure 1:
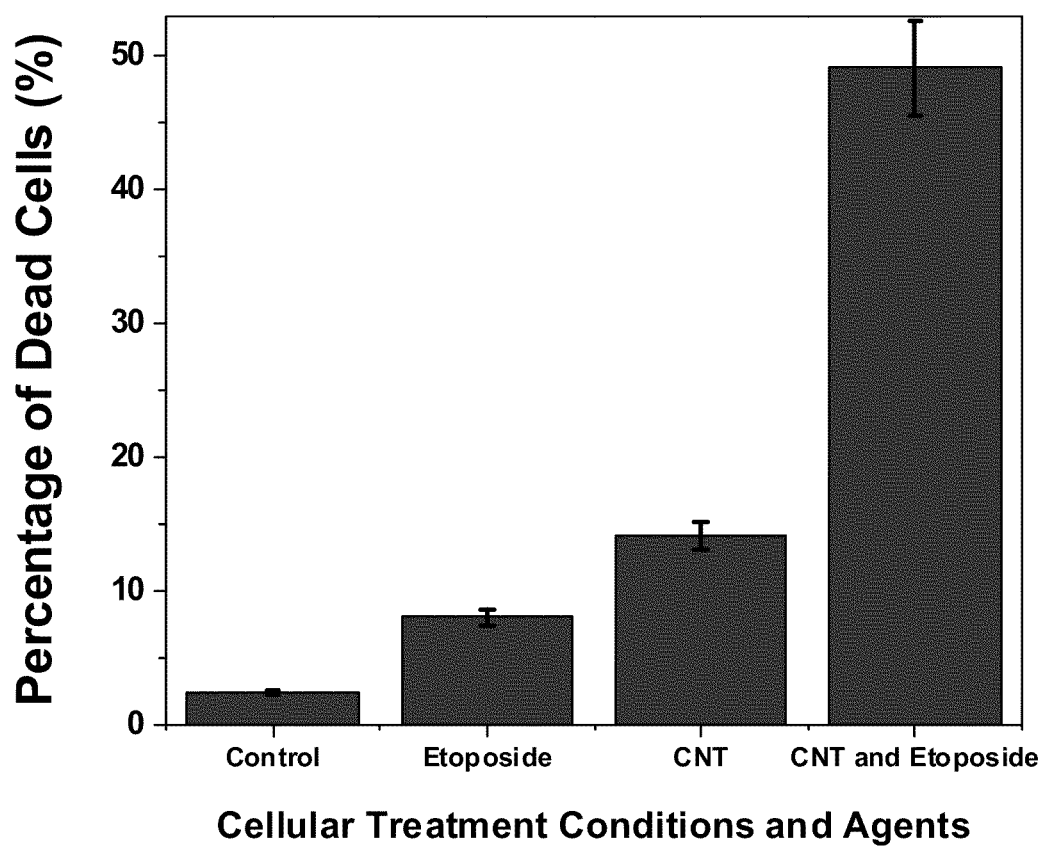
FIG. 1 is a bar chart showing the percentage of dead HeLa cells after exposure to etoposide, CNTs, and a combination thereof, compared to a control, wherein the cells were incubated for 24 hours with CNT (5 µg/ml), and an additional 6 hours with etoposide ($75 \times 10^{-6}$ M).

The interaction of various nanomaterials (silver and gold nanoparticles and single wall carbon nanotubes) with two different mammalian cell lines (osteoblast and cervical cancer) was evaluated in order to understand the impact of such materials on cellular morphology and biological functions. It was found that the nanomaterials induce morphological and cellular changes as they are being taken up by the cells. Additionally, it was found that the size of the cells changed based on the type of nanomaterials that they were exposed to and importantly some of their biological functions were found to be affected by the exposure to the nanomaterials. Investigation of the effect of several commonly used apoptotic agents in combination with different nanomaterials on several cellular functions indicated that the cells exposed to the combination of nanomaterials and apoptotic agents induced more cell death than when exposed to either agent individually. While not wishing to be bound by theory, this observation can be explained by the activation of caspase-3 pathways and therefore these findings could have a high potential for use in chemotherapy treatments of cancer. In such a case, the possible toxic effects of the nanomaterials can be used to synergistically enhance the percentage of cancer cells killed by the chemotherapeutic drugs.

According to some embodiments, a composition comprising nanoparticles and an apoptotic agent are described. The nanoparticles can be silver or gold nanoparticles or single wall carbon nanotubes (SWNTs). The compositions can be used as a treatment for cancer or to screen for compounds which exhibit synergistic behavior when combined with SWNTs. The nanostructures can act as bioactive molecules and promote the therapeutic action of the apoptotic agent through specific interaction with the cellular structures of malignant cells. According to some embodiments, the apoptotic agent is etoposide. According to some embodiments, the nanoparticles are not surface modified (e.g., surfaces of the single wall nanoparticles are not chemically modified after formation). According to some embodiments, the apoptotic agent is not conjugated (e.g., not covalently conjugated) to the nanoparticles.

The apoptotic agent can be any apoptotic agent. Exemplary apoptotic agents include, but are not limited to, etoposide and dexamethasone. Etoposide {systematic IUPAC name 4'-demethyl-epipodophyllotoxin 9-[4,6-O—(R)-ethylidene-beta-D-glucopyranoside], 4'-(dihydrogen phosphate), CAS No. 33419-42-0} is a cancer drug. It is well established that etoposide produces single and double strand DNA breakages and consequently delays progression through the late S or early G2 phase of the malignant cell cycle [18]. Moreover, etoposide induces oxidation-reduction reactions with the production of derivatives that bind directly to the DNA. As previously shown [19], this DNA damaging agent can trigger cell death through activation of p53-mediated caspase cell death signaling cascade [20]. The ultimate result of these molecular changes induced by etoposide is a process of self-destruction, in human malign cells. As described herein, the low response rate of Etoposide when used alone compared to the untreated HeLa cells (that is in line with earlier reports [21, 22]) is caused by the chemoresistance mechanisms activated inside the cells [23].

Apoptotic deficiency is one of the main mechanisms of chemoresistance to antineoplastic drugs. It has been shown that etoposide administration leads to the up-regulation of pro-apoptotic proteins such as Bax proteins [24,25]. These protein families translocate from the cytosol to the mitochondria being preceded by the release of the cytochrome-c that contributes to the induction of the mitochondrial permeability transition (MPT). This process is accomplished by the coupling of the DNA damages and leads eventually to the necrosis of the cells. The action of some cofactors in the cytoplasm like Apaf-1 (apoptotic protease activating factor-1; cytosolic protein involved in cell death), ATP/dATP, as well as the presence of some enzymes like pro-caspase-9, lead to the formation of the apoptosome complex in the cytoplasm, which activates caspase-9 that directs the activation of the caspase-3 proteins. Caspase-3 is one of 13 aspartate-specific cystein proteases that plays an important role in the execution of the apoptosis program and is primarily responsible for the cleavage of PARP (poly ADP ribose protease) during cell death and leads to the degradation and the fragmentation of the chromosomal DNA inside the nucleus and apoptosis inducement of the cell [26].

It has been shown that resistance to etoposide is due to molecular changes that affect apoptotic cascade at different levels [27]. Multiple mechanisms that block the activation of caspase cascade have been proposed in order to explain the acquired resistance of malign cells to etoposide [27]. Studies have reported that inactivation of Apaf1 is associated with chemoresistance in metastatic melanoma [28]. Other reports showed that activation of various caspases is required for p53-mediated apoptosis and chemosensitivity in cancer treatment, suggesting that measuring p53-dependent caspase activation may be useful to predict chemosensitivity in some cell types [29]. It was previously shown that targeting p53 for degradation by the human HPV E6 gene in the ovarian cancer cell line PA1 leads to an increase in the chemoresistant phenotype. Etoposide induces caspase 7 activation [30] and it was proved that an endoplasmic reticulum (ER) resident protein overexpression, GRP78 suppresses the activation of caspase-7 both in vivo and in vitro and consequently blocks the full activation of the multiple caspase-mediated cell death pathways in drug-treated cells, contributing to the development of drug resistance [23].

On the other hand, CNTs are known to induce cellular toxicity due to the accumulation of peroxidative products, oxidative stress, mitochondrial dysfunction and changes in cell morphology [31]. Several studies indicated different mechanisms of CNTs uptake inside the cells, and endocytosis is believed to be the most probable process [32]. Once the CNTs penetrate inside the cytoplasm or even nucleus, they are believed to strongly interact with the protein and DNA structures of the cells and therefore to enhance or limit various biological functions of the cells. Thus, endocytosis of CNTs can trigger their binding to intracellular targets, which could cause the altering of cellular signaling, motility, and metabolism, affecting the mechanisms of chemoresistance, especially cell-cycle mediated drug resistance.

Figure 5:
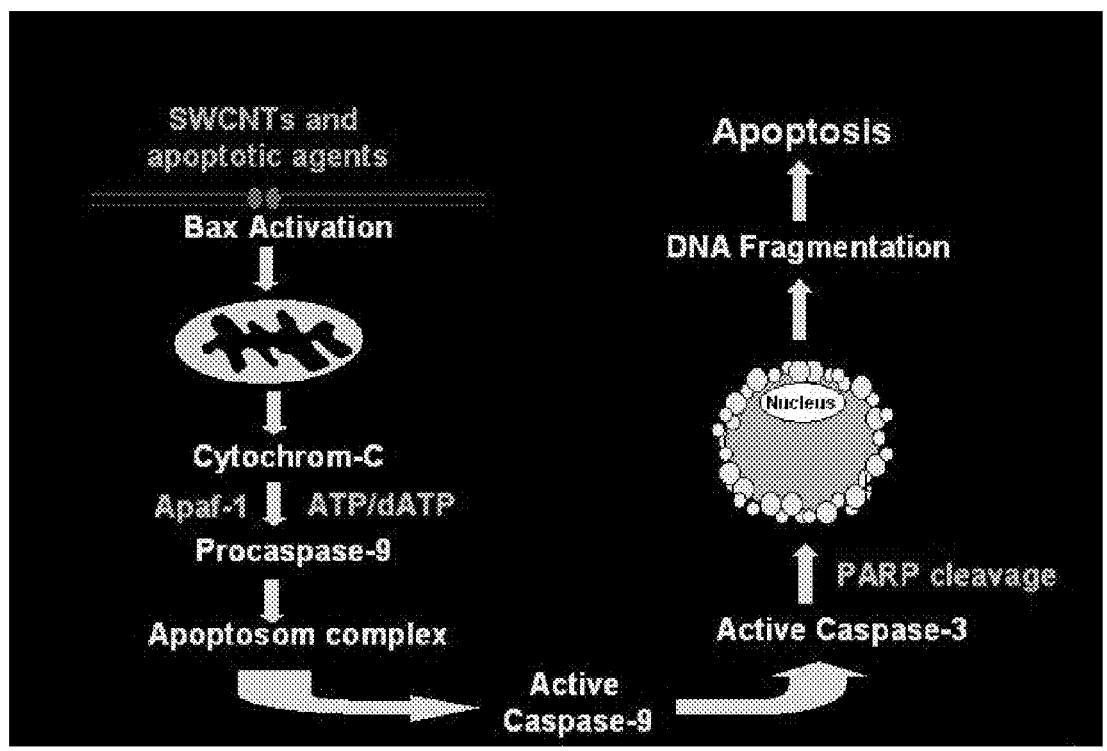
FIG. 5 is a schematic illustrating proposed mechanisms for the combined action of Etoposide and CNTs for the induction of apoptosis, which leads to cellular death.

The first response of the cell in contact with CNTs is represented by the induction of antioxidant and detoxification enzymes followed by inflammation, which is a result of the activation of pro-inflammatory signaling cascade [33]. The most common such responses are the generation of mitogen-activated protein kinase (MAPK) and nuclear factor kB (NF-kB) cascades. The ultimate response is represented by mitochondrial perturbation, activation of caspase cascade and release of pro-apoptotic factors that leads to cell death. Thus both agents can induce apoptosis with some similar pathways, which can interact and provide synergy in final results leading eventually to cells death as combination of apoptotic and necrotic phenomena. Some hypothetical processes with focus on apoptosis are depicted in FIG. 5.

The synergistic therapeutic potential of the combination of an apoptotic agent (e.g., etoposide) and CNTs has been demonstrated. The therapeutic efficacy of the combination is particularly pronounced compared to the relatively poor efficacy of etoposide as an apoptotic agent when used individually. While not wishing to be bound by theory, based on these results it is believed that the CNTs initiate the apoptotic cascade via caspase pathways and interfere with resistance mechanisms at this level enhancing the apoptotic affect of etoposide. Eventual rapid shifting from early to late apoptosis and undergoing necrosis lead to cell death. The contribution of the "snaking" effect of CNT filament during their crossing of cellular membranes, which could provide larger amounts of etoposide penetration inside the cells, cannot be excluded. Nor is it likely that etoposide can enhance toxic effects of CNTs although theoretically it is quite possible. Nevertheless, the demonstrated approach may shift the toxicity of nanostructures from a drawback to an advantage for in-vivo applications. In particular, it was recently proposed that the tumor targeting laser-induced removal of the protective coating around toxic nanomaterials (e.g., quantum dots) may be considered as another potential killing mechanism associated with increased local toxicity [34].

Compositions comprising both CNTs and an anti-cancer agent such as etoposide provide for the development of novel hybrid drugs that contain both nanostructural materials as well as apoptotic substances for the treatment of cancer.

Although etoposide is exemplified above, any apoptotic agent or anti-tumor drug can be used in combination with the nanoparticles. The nanoparticles can be conjugated (e.g., bioconjugated) to various targeting molecules including, but not limited to, antibodies, growth factors, folates, fragments of antibodies and synthetic targeting molecules. The nanomaterials and the chemotherapeutic agents can be delivered simultaneously or sequentially. The nanomaterials can be coated with various coatings to enhance their bio-compatibility and/or to provide functional groups for the attachment of the apoptotic agents. A single type of nanoparticle or a combination of different nanoparticles can be used. A single apoptotic agent or a combination of apoptotic agents can be used in combination with one or more different types of nanoparticles. The apoptotic agent and nanoparticles can be placed into a container that delivers the contents of the container into the tumor. The nanoparticles can be particles with one or more dimensions of 100 nm or less.

Experimental

The practice of this invention can be further understood by reference to the following examples, which are provided by way of illustration only are not intended to be limiting.

The action of etoposide and CNTs on HeLa cancer cells as single and combined therapy was studied. A highly increased anti-tumor activity of combinations of Etoposide and CNTs was observed compared to the single administration of each agent, which suggests that the CNTs can alter the mechanisms of chemo-resistance in malign cells. These findings provide the potential for new treatment approaches and improvement of current cancer therapies by using both cytostatic and nanostructural materials (such as CNTs), which synergistically are more aggressive and possess greater curative rates in the treatment of cancer.

Single wall carbon nanotubes (hereinafter referred to as "CNTs") were grown by Radio-Frequency Chemical Vapor Deposition (RF-CVD) on a Fe:Mo/MgO catalyst with methane as the carbon source. After purification, the purity level of the nanotube samples was 99%. The CNTs were freshly sonicated with the cell growth medium just before introducing them to the cell cultures. The concentration of the CNTs was determined by UV-Vis-NIR spectroscopy and Atomic Force Microscopy (AFM).

Cell Cultures

Human cervix adenocarcinoma, HeLa, cells were obtained from the American Type Culture Collection and maintained using established procedures. Cells were normally grown in 75 cm² flasks (density of 106) with F-12K medium containing 10% fetal bovine serum (FBS), 1% penicillin (500 units/ml) and streptomycin (500 units/ml) at 37° C. in 5% $CO_2$ atmosphere then subcultured by trypsinization for further experiments. The cells were kept in aseptic conditions and the media was changed every 48 hours.

Treatment Protocol

The cells were seeded at a density of $1 \times 10^4$ cells/well in 48 well plates. Following treatments with CNTs, the combined action was studied by adding appropriate volumes of etoposide or vehicle as control to obtain the desired final concentrations. Incubations continued for additional 6 hours before staining or harvesting the cells for further analysis. Stock solutions of Etoposide ($75 \times 10^{-6}$ M) and CNTs (5 µg/ml) were prepared and delivered separately and together to the cell cultures for treatment. All treatments including controls were performed in triplicate samples.

Cell Assessment with Light Microscopy

For microscopic studies, cells were grown on 35 mm plates at a density of $25 \times 10^4$ cells/dish and supplemented by the CNTs. Following incubation methods above, the cells were washed thoroughly with 10 mM phosphate buffered saline (PBS, pH 7.4) 3 times and then fixed with 10% formaldehyde solution for 10 min, washed 3 times with PBS and stained with Methyl Green dye for 10 min. The cells were monitored by light transmission microscopy using an Olympus BX 51 microscope.

Cell Viability Analysis

The percentage cell viability was measured by Trypan blue dye. First, the cells were cultured as described above for 24 hours and exposed to various treatments. The cells were then dissociated from the bottom of the plate by trypsinization and transferred to 1.5 eppendorf tubes and centrifuged. Finally, 25 µL of 1× Trypan blue dye was added to each sample and incubated for less than 5 min. The number of viable cells was counted using a hemacytometer.

Caspase-3 Assay

Caspase-3 assay was used for the assessment of possible apoptosis and it was performed using the Biovision Gasp-GLOW Red Active Caspase-3 staining kit. The HeLa cells were incubated with and without the CNTs overnight. The assay agent was then added and incubation continued for additional 6 hrs. The cells were collected by scrapping and were transferred to 1.5 eppendorf tubes, incubated with 1 µl of the Red-DEVD-FMK for 1 hour at 37° C. with 5% $CO_2$, and then centrifuged for 5 minutes at 3000 rpm. The supernatant was removed carefully and the cells were resuspended in 50 µl of buffer and centrifuged again. Finally, the cells were resuspended in 100 µl of the washing buffer and a few drops of the cell suspension were transferred to the microscopic slides in order for the brightness of the red stain to be measured and analyzed. The brightness level of the red stain indicates the caspase-3 activation level in the cells.

Flow Cytometry

Flow cytometry was performed following staining of cells with YO-PRO-I and PI dyes from a Vybrant kit #4 (V-13243, Molecular Probes) to assess both apoptotic and necrotic cells. The cells were seeded at a density of $1 \times 10^6$ cells/25 cm² culturing flask. DMSO was used as vehicle control while etoposide was used as the positive control for analyzing the combined effect of the Etoposide-CNT treatment. After 6 hrs of additional treatment, cells were trypsined and washed twice with cold PBS, pH 7.4. Aliquots of 1 µl YO-PRO-I stock solution (component A) and 1 µl PI stock solution (component B) were mixed per ml of cell suspension. After 30 min incubation at 4° C., the cells were analyzed using a BD FacsCalibur flow cytometer to sort out the cells undergoing apoptosis or necrosis from normal population based on labeling with each fluorescence probe. Fluorescence emissions were measured at 515-545 nm for FITC using FL-1 PMT detector and 564-606 nm for PI using FL-2 PMT detector.

Statistical Analysis

All data were expressed as mean±SD. Independent sample t-test was performed for 2 group comparisons. P values of 0.05 or less were considered to indicate significance.

Results

Figure 2:
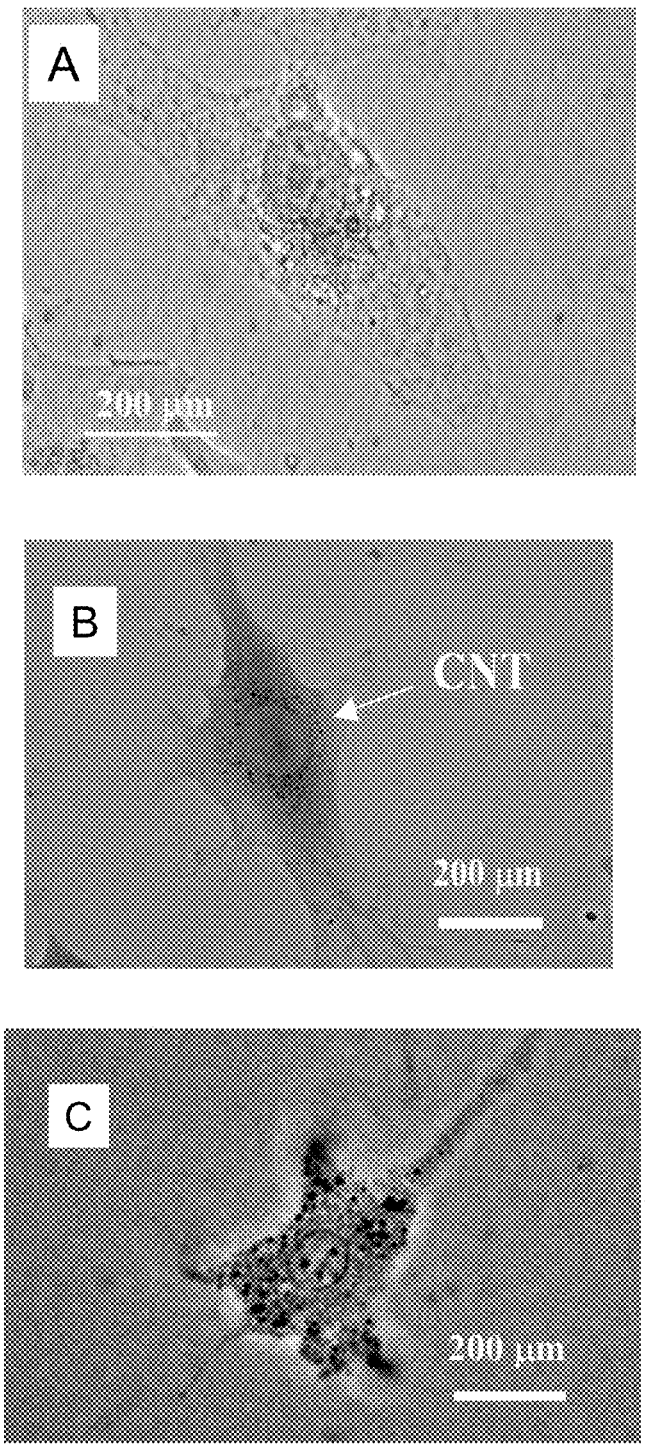
Figure 3A:
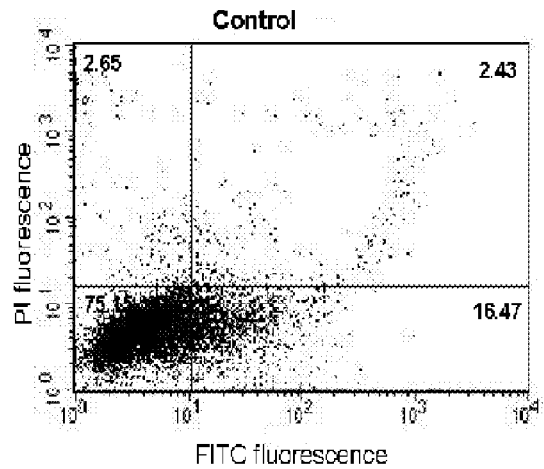
FIGS. 3A-3D are flow cytometry data indicating the effect of DMSO (as vehicle control) ($75 \times 10^{-6}$ M), CNTs (5 µg/ml, 24 hours) and etoposide ($75 \times 10^{-6}$ M, 6 hours) as mono- and combined therapy of the HeLA cells, wherein cells were stained with YO-PRO-I and PI dyes from Vybrant viability assay following manufacturer's instructions and analyzed by flow cytometry and wherein live (FIG. 3C), apoptotic (FIG. 3D) and necrotic cells (FIGS. 3A and 3B) are shown.
Figure 3B:
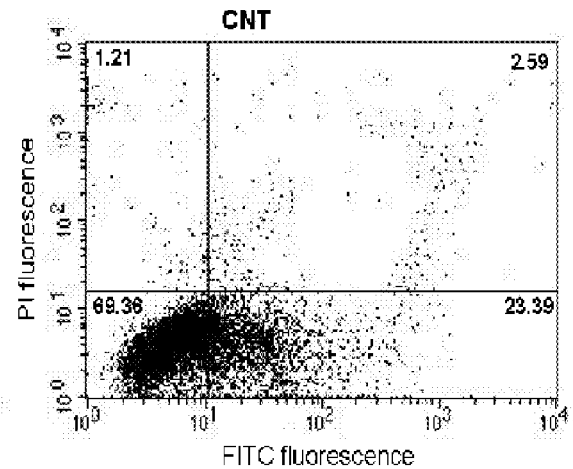
Figure 3C:
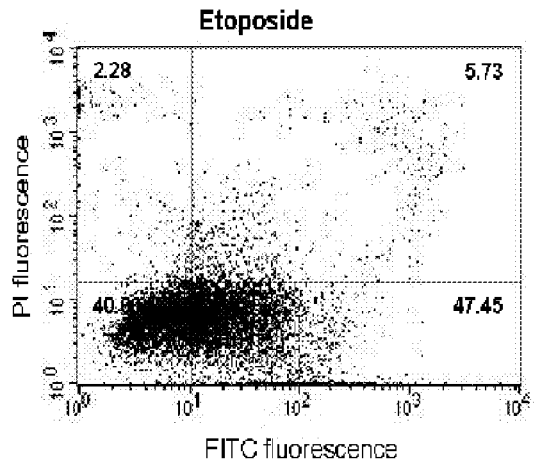
Figure 3D:
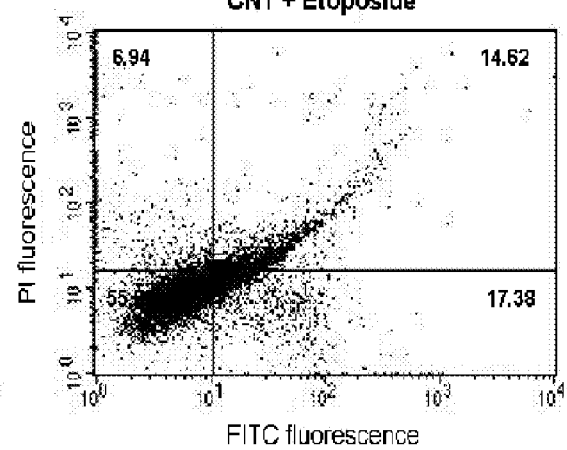

The trypan blue assays revealed (FIG. 1) a relatively low percentage of dead cells in culture medium at level 2.26±0.45%, while administration of CNTs alone led to the increase of the cellular death rate to 14.1±2.1%. Compared to the control experiment, the CNTs increased the relative rate of the death cells by 11.84±1.4%. The death rate of the HeLa cells after the etoposide administration was of 7.8±1.87% and therefore etoposide increased the death rate of HeLa cells by 5.54±1.34% over controls. The incubation of the HeLa cells with CNTs and etoposide at identical doses as when incubated with each of the two agents individually showed a significantly higher cell death rate of 49.1±1.5%, resulting in an increase by 46.84±2.3% rate over controls (FIG. 1). Thus the combined effect was approximately 2.7-fold higher ($p<0.05$) than the sum of individual effects of CNTs and etoposide (17.38±1.2%). The optical images of single HeLa cells in FIGS. 2A-2C illustrate that the administration of CNTs alone do not change the cell morphology compared to the control (intact) cells while the combined action led to a significant change of cellular morphology. It includes nuclear shrinking, nucleus fragmentation, and membrane modification, which are the typical signs of apoptosis. Cells swelling as wholes indicate also the appearance of necrotic phenomena.

Figure 4A:
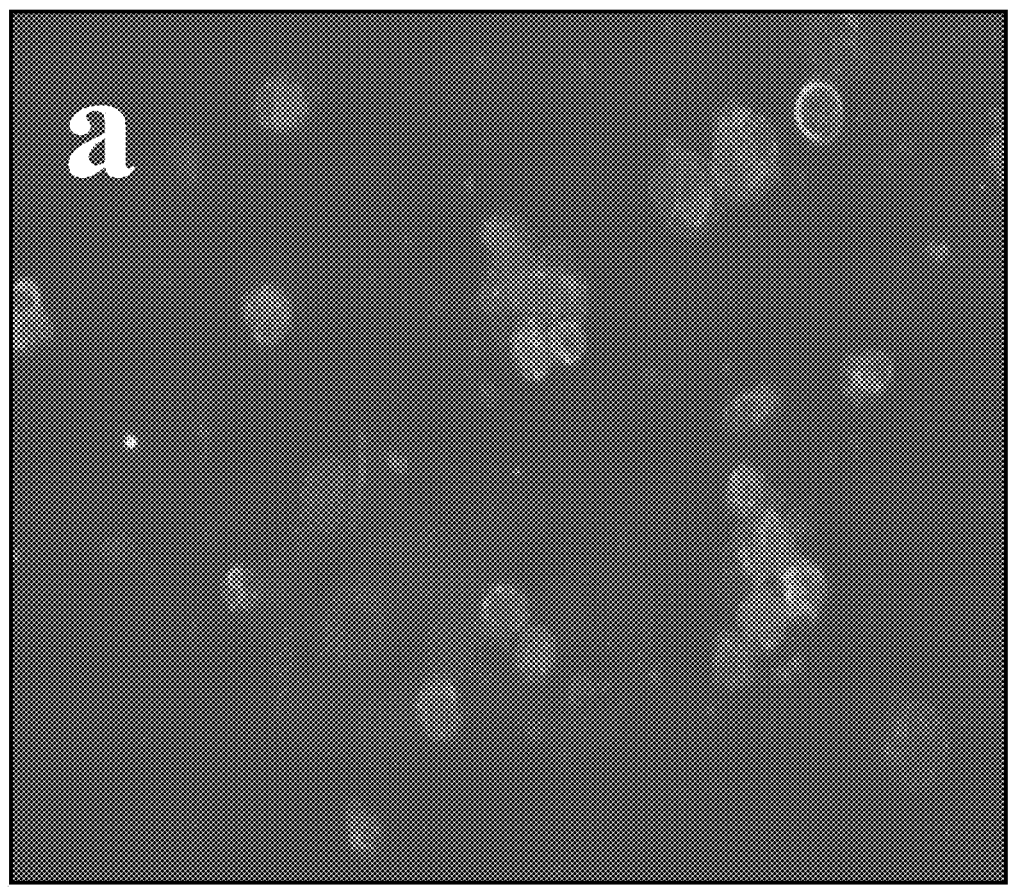
FIG. 4A shows a control sample (i.e., unexposed to any agents)
Figure 4B:
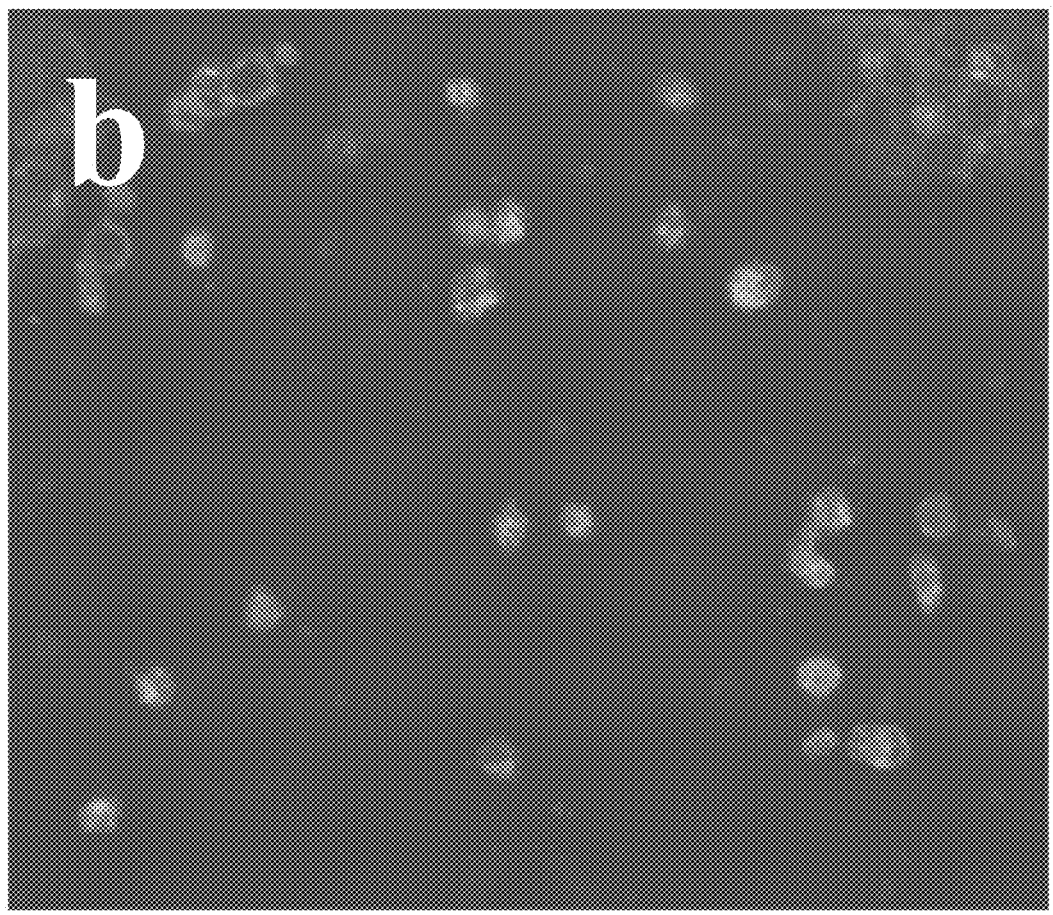
FIG. 4B show samples exposed to CNTs (5 µg/ml, 24 hours)
Figure 4C:
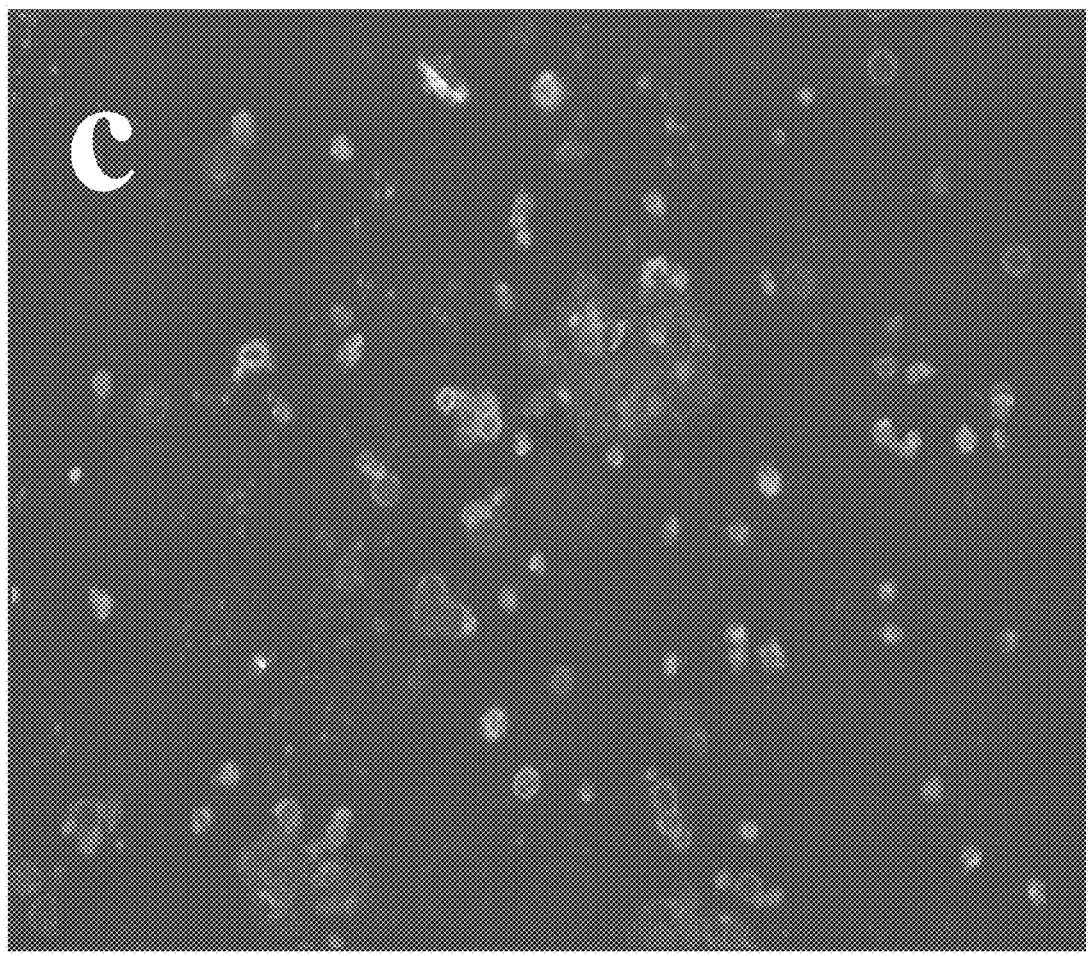
FIG. 4C shows samples exposed to a combination of CNTs and Etoposide ($75 \times 10^{-6}$ M, 6 hours).

To confirm these observations with relatively simple viability assay, we further verified apoptotic and necrotic effects of etoposide, CNTs, and their combination using flow cytometry analysis with specific fluorescent labeling that allows to differentiate between apoptosis and necrosis. FIG. 3 shows that the treatment of HeLa cells with etoposide and CNTs alone, enhanced apoptosis as compared with DMSO (used as vehicle control) with more profound effects for etoposide. Both agents induced slight levels of necrosis, which is more statistically significant for etoposide. However, the combined treatment of CNTs with etoposide drastically increased the population of dead cells undergoing late stages of apoptosis or necrosis (upper left and upper right quadrants), which was not achieved by treatments with either etoposide or CNTs alone. Apparently CNTs enhance etoposide treatment by shifting (likely rapid) early apoptotic cells into late apoptotic cells that further undergo necrosis. These results provide evidence that CNTs-etoposide combination therapy can achieve better results of cell death and thus eliminate carcinogenic cells. To confirm enhancement of apoptosis, these results were further verified by assessment of the Caspase-3 activity performed by staining the cells with Red-DEVD-FMK (Method section). The control cells showed a weak fluorescence for the Caspase-3 analysis, but it became significantly brighter for the cells incubated with the CNTs alone (FIG. 4). Therefore the CNTs were found to induce a higher death rate in cells and to have a strong interaction with the cells via caspase pathways, which is typical for etoposide action [16, 17]. Thus, when the cells were incubated with the combination of CNTs and etoposide, the caspase-3 activity expressed by the Red-DEVD-FMK labeling was evidently very high, clearly indicating that the administration of both Etoposide and CNTs enhance and activate apoptosis through the caspase cascade.

Additional Experiments

Additional studies were conducted to study the potential cytotoxic effects of several types of nanomaterials for two types of cells: normal, noncancerous (bone MLO-Y4 Osteocytic cells) and abnormal, cancerous (cervical cancer HeLA cells). These cell lines were used because of previous results indicating that MLO-Y4 cells behave normally in culture and express certain mineralization functions that are indigenous to their tissue of origin and HeLa cells because they are model cancer cells used throughout the cancer literature to understand how abnormal cells behave in culture. The experiments were conducted to determine the cytotoxic responses in the normal cells and to see if the potential toxic effects of the nanomaterials can be used to kill cancer cells especially when used in conjunction with commonly used chemotherapeutic drugs. Therefore the studies were done in parallel on cancer and non-cancer cells to analyze the differences in the cellular morphology and functions due to the nanomaterials. In order to fully understand these cellular changes we have evaluated the size of the cells, the apoptotic rate and the possible activation of the caspase family proteins, which are an indicator of the death process of the cells. These studies were designed to understand the possible benefits that can be obtained in destroying cancer cells using nanomaterials and to understand their potential cytotoxic effects on normal and cancer cells in culture. A variety of morphological endpoints were evaluated including alteration of cell size and shape because, in homogeneous cell populations of cultured cells, these traits are generally considered initial indicators of toxicity.

MATERIALS AND METHODS

Nanoparticles Synthesis

Figure 6A:
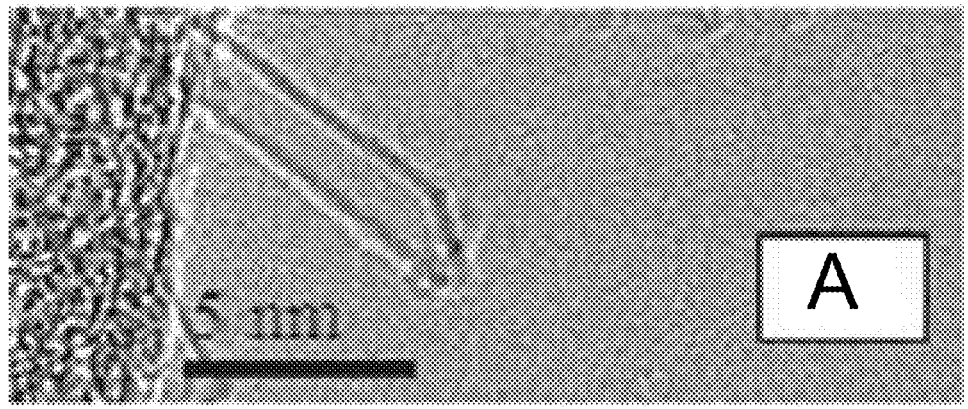
FIG. 6A is a high-resolution TEM image of carbon nanotubes.
Figure 6B:
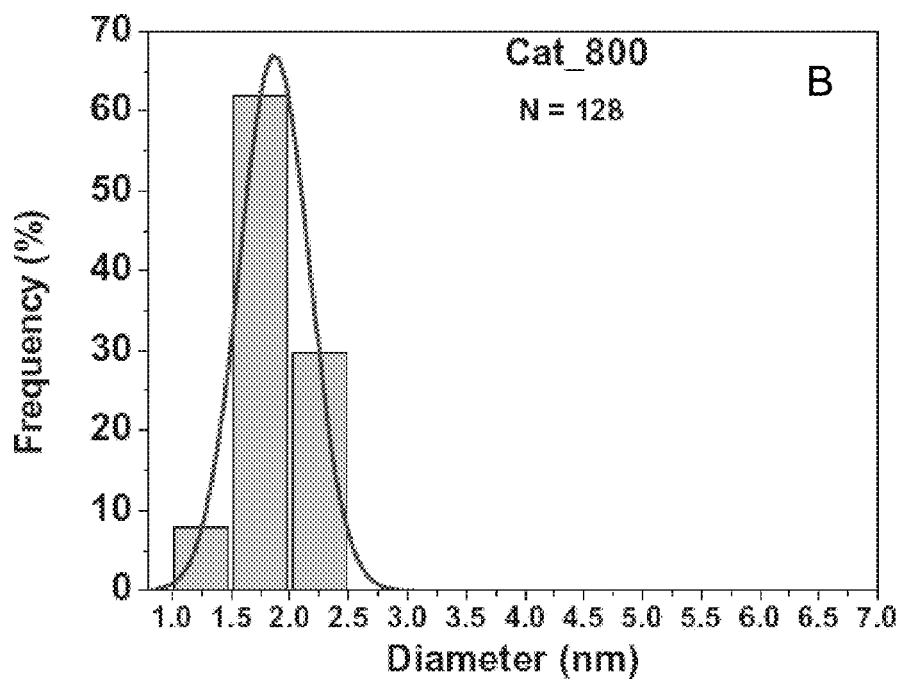
FIG. 6B is a graph showing the diameter distribution of the carbon nanotubes of FIG. 6A after measuring 128 of the carbon nanotubes.

Single-wall carbon nanotubes were grown by Chemical Vapor Deposition process using a Fe:Co:MgO catalytic system. The catalyst with a stoichiometric composition of 2.5:2.5:95 wt %, was prepared by the impregnation method as follows: first, the weighted amount of metal salts, $Fe(NO_3)_3 \cdot 9H_2O$ and $Co(NO_3)_2 \cdot 6H_2O$, were dissolved separately in ethanol with agitation. Next, freshly calcinated (500° C. for 2 h) MgO was dispersed into 30 ml of ethanol and the metal salt mixtures were added to the MgO solution. The final mixture was sonicated for about 1 h. Next, the ethanol was evaporated under continuous agitation, and the catalyst system was further dried overnight at 60° C. Finally, the catalyst was calcinated in air at 500° C. for about 2 h. Single wall carbon nanotubes (SW-CNTs) were grown by radio frequency (RF) catalytic vapor deposition (CCVD) on the bi-metallic catalyst system Fe—Co supported on MgO, utilizing methane as a hydrocarbon source. About 100 mg of the catalyst was uniformly spread into a thin layer onto a graphite susceptor and placed in the center of a quartz tube with inner diameter of 1 inch. First, the tube was purged with the carrier gas (Argon) for 10 min at 150 ml/min. Next, the RF generator was turned on and, when the temperature of the graphite boat reached the desired synthesis temperature, methane ($CH_4$) was introduced at 40 ml/min for 30 min. The temperature at which the nanotubes were grown was varied between 700 and 1000° C. at 50° increments. At the end of each reaction, the system cooled down under the presence of Argon for 10 min. This same procedure was followed for the heat treatment of the catalyst system at 800 and 1000° C. respectively. In this case, the samples were heated and cooled down under argon atmosphere without introducing the hydrocarbon. The weight of the catalyst was measured before and after the blank reactions. The as-produced CNTs were purified in one easy step using diluted hydrochloric acid solution and sonication. To burn the amorphous carbon, the purified samples were heated in air at approximately 400° C. for about 15 min. FIG. 6 shows a high-resolution TEM of the nanotubes used for this study as well as their corresponding diameter distribution after analyzing 128 nanotubes.

SW-CNTs were added to the growth medium prior to cell culturing and the resultant fluid was sonicated to distribute the particles uniformly. The concentration of nanoparticles was determined by UV-vis-NIR spectroscopy and atomic force microscopy (AFM) techniques.

Figure 7A:
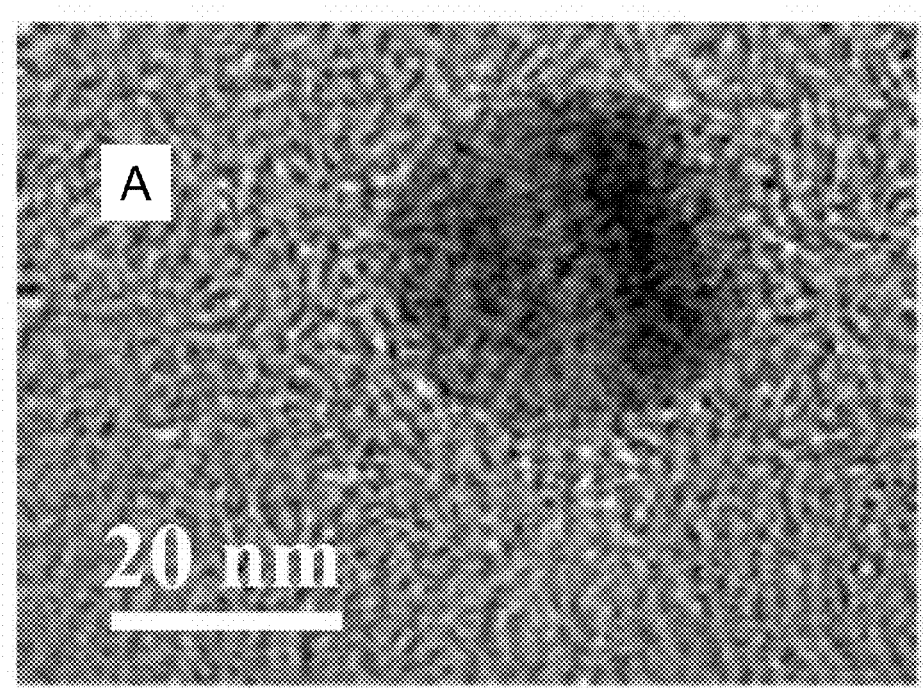
FIG. 7A is a high-resolution TEM image of silver nanoparticles.
Figure 7B:
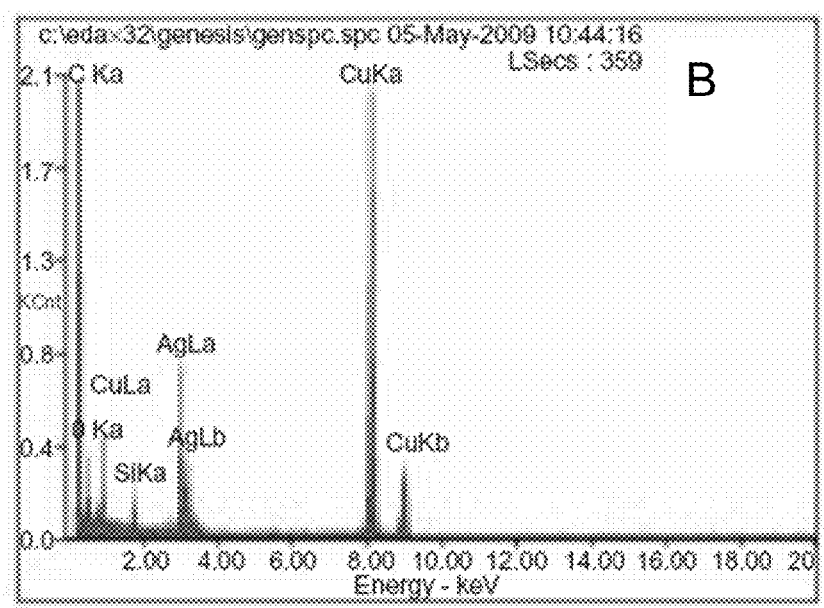
FIG. 7B illustrates the elemental analysis of the silver nanoparticles of FIG. 7A wherein the presence of Ag can be seen along with Cu and C, which are due to the grid and analysis process.
Figure 7C:
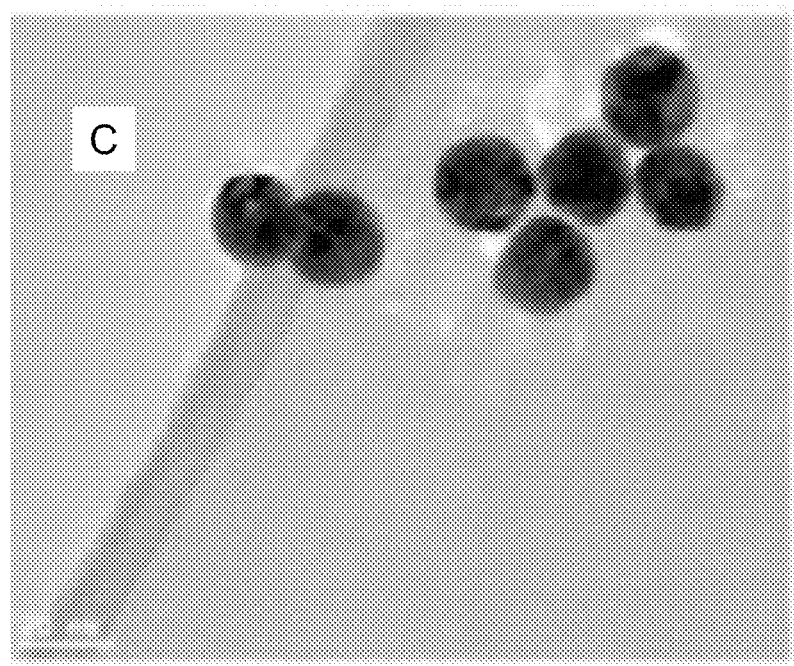
FIG. 7C is a high-resolution TEM image of gold nanoparticles.
Figure 8A:
FIG. 8A shows cells cultured with appropriate growth medium only.
Figure 8B:
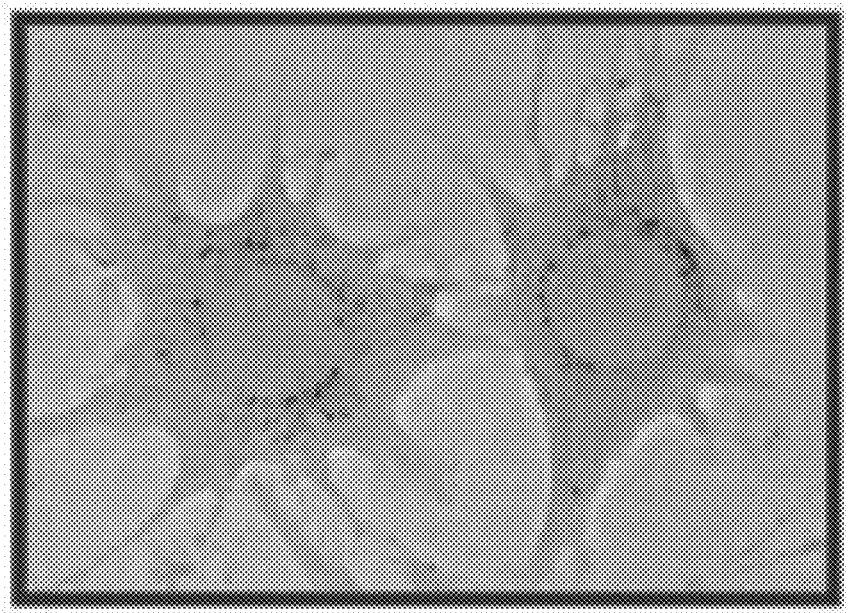
FIG. 8B shows cells cultured with gold nanoparticles.
Figure 8C:
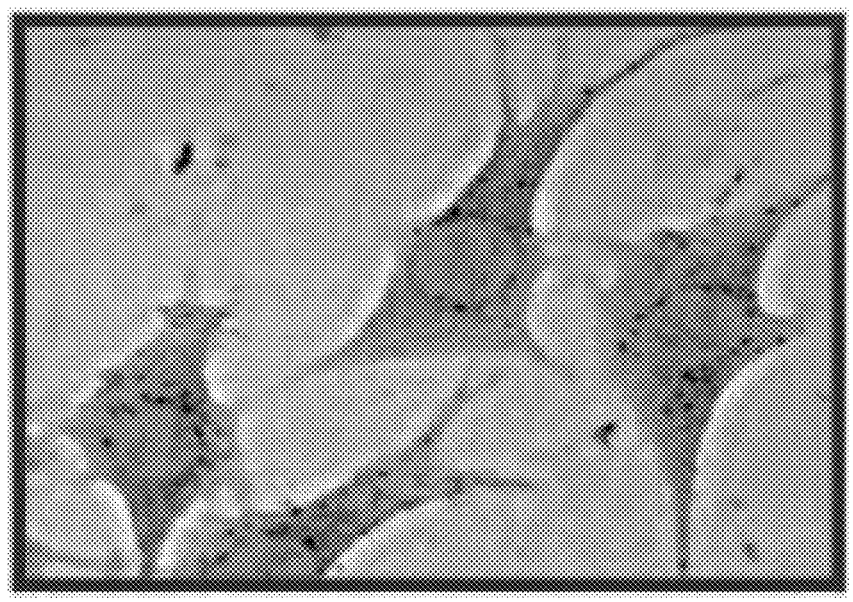
FIG. 8C shows cells cultured with silver nanoparticles and FIG. 8D shows cells were cultured with single wall carbon nanotubes.
Figure 8D:
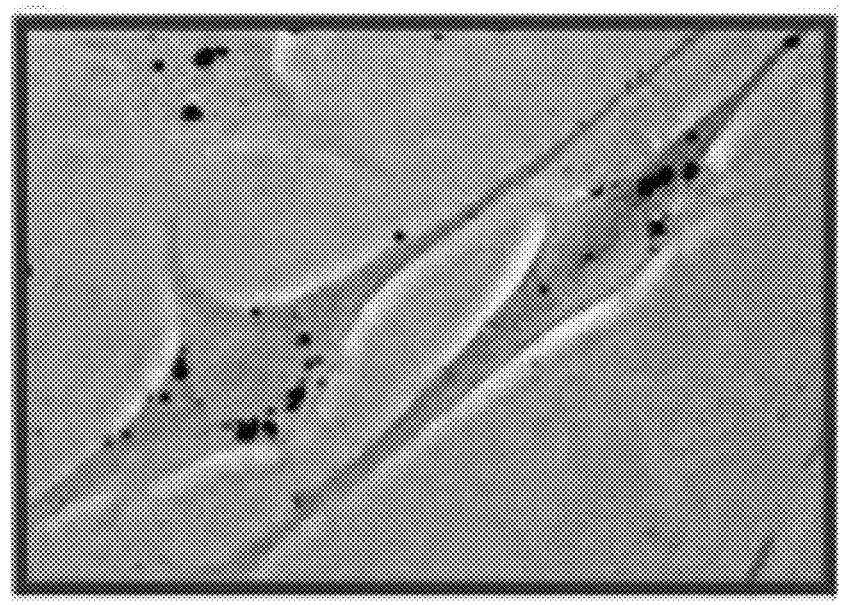

Silver NPs (purity of 99.999 wt %) with the average diameter of 23.0±2.0 nm (80.4±1.0% of peak intensity) and the peak width of the nanomaterial at half-height of 7.1±1.5 nm were prepared by borohydrate-mediated reduction of silver nitrate and was based on the following protocol: in deionized (DI) water sodium borohydrate was introduced followed by sodium citrate followed by $AgNO_2$ (drop wise) under slow stirring. Polyvinyl pyrrolidone (PVP) was added to the solution and the mixture was stirred for 30 min. The resulting product was a golden yellowish in color. The high magnification TEM image and the elemental analysis of the silver nanoparticles are shown in FIGS. 7A and 7B, respectively. Gold nanoparticles 20 nm (purity of 99.999 wt %) were purchased from (Sigma Aldrich company, product number G1652-25ML) and they contained ~0.01% $HAuCl_4$, with a concentration of ~1 A520 units/ml. The average size of the monodisperse nanoparticles was 20 mm and the diameter was found to vary between 17 and 23 nm mean particle size. A high-resolution TEM image of the gold nanoparticles is shown in FIG. 7C.

Cell Culturing

MLO-Y4 osteocytic cells obtained from murine long bone were grown on collagen-coated tissue culture plates at 0.5× $10^6$ cells/10 cm tissue culture dish. The cells were maintained with alpha-modified essential medium supplemented with 2.5% fetal bovine serum, 2.5% calf serum and 1% penicillin, streptomycin and gentamycin antibiotics [4 mM L-glutamine and 100 U/ml of each penicillin and streptomycin (PS)]; HeLA cells ($1\times10^6$) were grown in 75 $cm^2$ flasks with minimum essential medium supplemented with 10% fetal bovine serum and 1% PS. For the stock culture both cell lines were incubated for several days using a humidified incubator (37° C., 5% $CO_2$).

Nanomaterials Administration

Single-wall carbon nanotubes (SW-CNTs) were delivered to the cell cultures by sonicating them for 1 h into the medium used to feed the cells. Silver (Ag-NPs) and gold (Au-NPhs) nanoparticles were centrifuged at 9000 rpm at 4° C. for 2 h; culture medium was mixed with NPs solutions at a concentration of ($10^{-12}$ and $0.5\times10^{-9}$ M). Stock cultures were trypsinized and transferred to 48-well plates in a desired density of $10^4$/well and incubated overnight under the same conditions with the nanomaterials.

Apoptosis Induction

MLO-Y4 osteocytic cells were used for apoptosis induction assay. Solutions of dexamethasone ($1\times10^{-6}$ M), etoposide ($75\times10^{-6}$ M) and cell culture vehicle only (ethanol and DMSO) were separately administered to the cell cultures. Incubation for 6 h was performed. Experiments also included three control samples with exposure only to cell culture vehicle, dexamethasone or etoposide, respectively.

Characterization of the Cells

Cells from the same passages were grown on 35 mm plates in a density of ($25\times10^4$ cells/dish) and supplemented with the nanomaterials as previously described. The cells were washed thoroughly with 1× phosphate buffered saline solution (PBS) three times and then fixed with a 10% formaldehyde solution for 10 min, washed three times with PBS and stained with Methyl Green dye for 10 min. The cells were monitored by using an optical microscope and their size was measured and analyzed statistically.

Cells Viability Analysis and Trypan Blue Assay

The percentages of dead and alive cells were determined by Trypsan Blue exclusion, a standard method to detect cell death. The cells were cultured for 24 h with different nanomaterials at the concentrations already cited in the appropriate growth medium in a 48-well plate in a desired density, as previously described. Then, the cells were dissociated with trypsin and transferred to 1.5 Eppendorf tubes and centrifuged. Finally, 25 µl of 1× Trypsan Blue dye was added to each sample and incubated for less than 5 min. The viable cell number was counted using a hemacytometer, and the viability values were derived by the following equation. These values were compared to the negative control.

Percentage of dead cells={no. of dead cells(%)/(no. of alive cells+no. of dead cells)}×100

Caspase-3 Activity Assay

Caspase-3-like assay was done with the caspase-3 assay kit (Biovision Inc.). Briefly, apoptosis was induced with the desired methods by culturing HeLa cells with and without the nanoparticles overnight and the apoptotic agents were added and incubated for 6 h. The cells were collected using a scraper and transferred to the 1.5 Eppendorf tubes and incubated with 1 µl of the Red-DEVD-FMK, incubated for 1 h at 37° C. with 5% $CO_2$, centrifuged for 5 min at 3000 rpm and the supernatant removed carefully. The cells were resuspended with 50 µl of the washing buffer and centrifuged again; finally the cells were resuspended with 100 µl of the washing buffer and a few drops of the cell suspension were transferred to the microscopic slides and the brightness of the red stain was assessed visually. The brightest red cells had the active caspase-3 while the less red stained cells have the less activated caspase-3.

Statistical Analysis

All data were expressed as means±SD. Differences among three or more groups were evaluated by means of one-way ANOVA test and independent-sample t-test was performed for two-group comparisons. P-values of 0.05 or less were considered to indicate significance.

EXPERIMENTAL RESULTS

Effects of Nanoparticles on Osteocytic Bone Cell

Morphology

Figure 9:
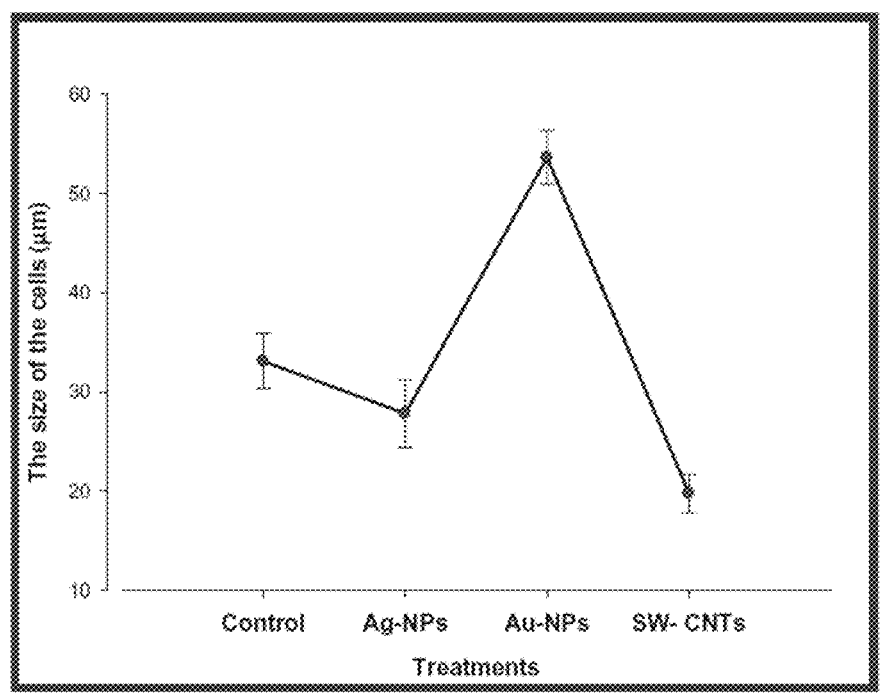
FIG. 9 is a graph showing the effect of the nanomaterials on osteocytic bone cell morphology wherein the osteocytic bone cells were incubated with $0.5 \times 10^{-9}$ M of Au-NPs, Ag-NPs and SW-CNTs overnight and the data collected from 24 cells/sample for four experiments and wherein the data shown is the mean of the size±standard deviation.
Figure 10A:
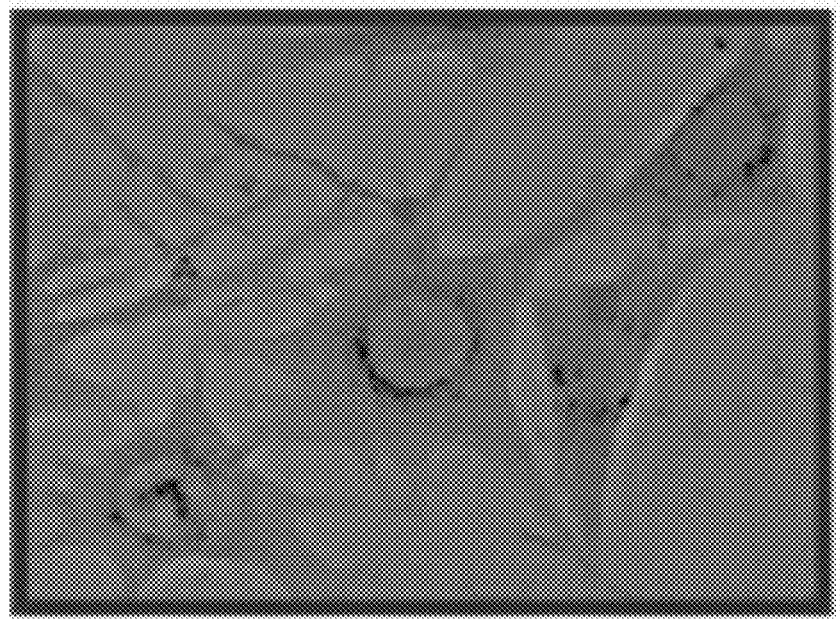
Figure 10B:
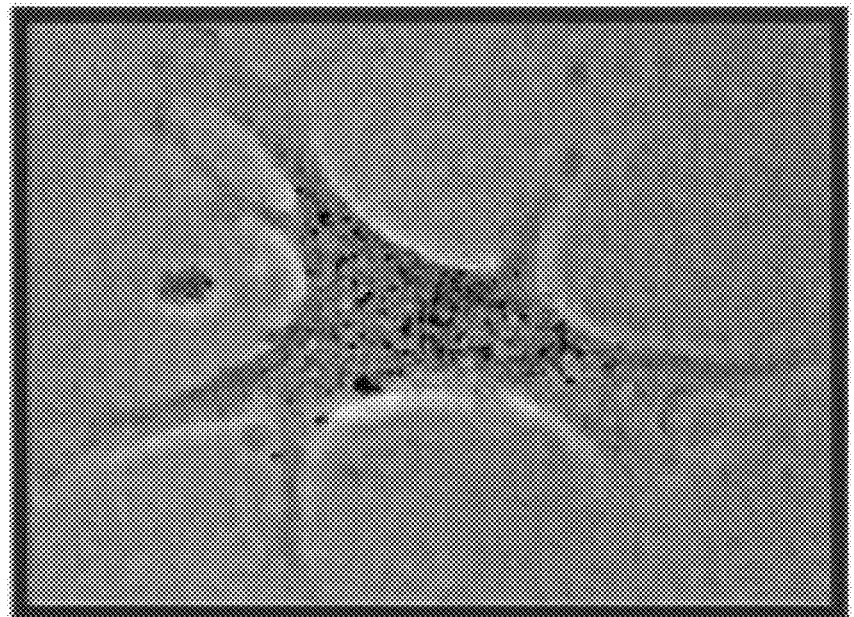
Figure 10C:
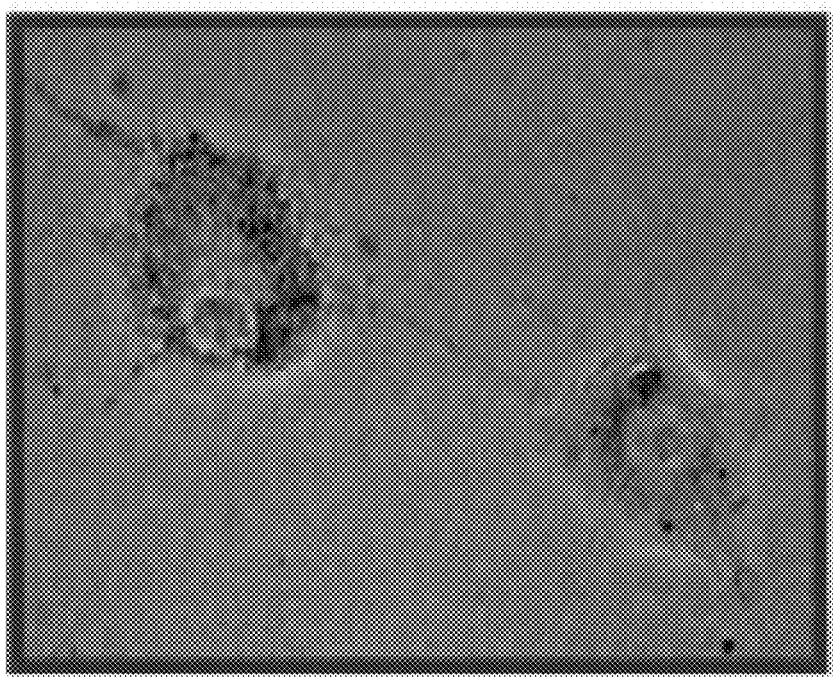
Figure 10D:
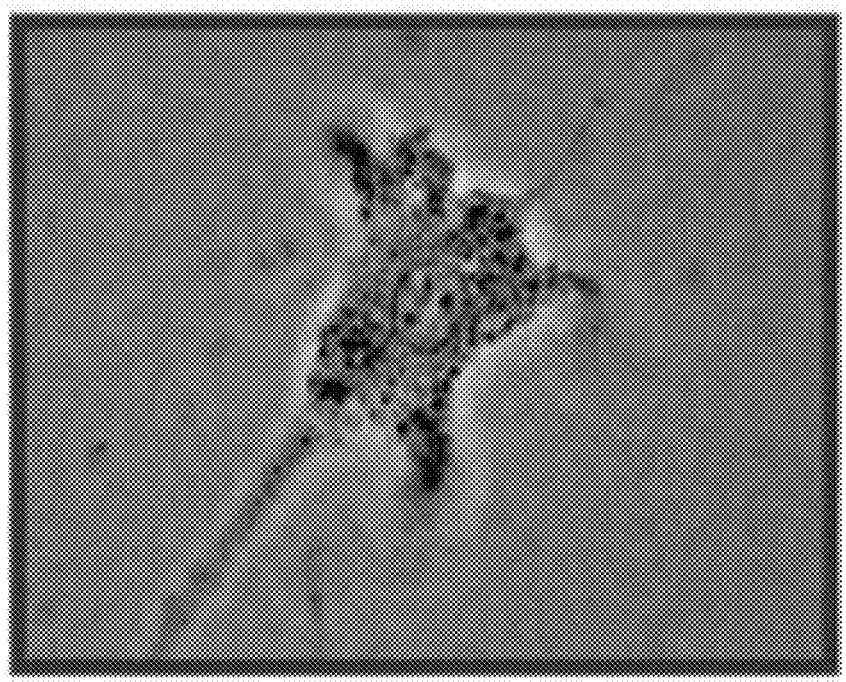

Four separate studies were performed in which 24 cells/sample were analyzed for each experiment, in order to obtain statistical valid information. The first experiment consisted of exposing cells to the appropriate growth medium only. For the next three experiments, silver nanoparticles, gold nanoparticles of (10-20 nm) and SW-CNTs were mixed into the growth medium at a concentration of $0.5\times10^{-9}$ M and dispersed by sonication for 1 h before being administrated to the MLO-Y4 osteocytic bone cells. FIG. 8 illustrates cellular shape and morphological changes observed during the nanomaterials delivery experiments. Administration of SW-CNTs induces elongation of cells while gold and silver nanoparticles did not appear to alter the spherical morphology of the cells. Different cell size changes were observed according to the administered nanomaterial (FIG. 9). Differences among the four groups were significant ($P<0.05$), with the largest cell diameter observed in Au-NPs (53.63±2.52 µm), followed in descending order by controls (33.1±2.76 µm), Ag-NPs (27.82±2.99) and SW-CNTs-administered cells (19.77±1.28 µm). The nanoparticles translocation into cells in vitro most probably happened due to processes such as diffusion, transmembrane channels or adhesive interactions. The factors affecting this process were found to be the surface charges of the nanoparticles, particle types and sizes. The size was found to be the most important factor for the cells' modifications. The cellular size changes due to uptake of nanomaterials can be explained by the potential of the nanoparticles to develop small openings in the cell membrane that would allow a more significant liquid exchange with the outside medium or because of a physiological response to intracellular location of the nanomaterials.

Effects Induced by Nanomaterial Concentration

In a separate set of experiments, the nanoparticles were delivered to the MLO-Y4 cells at various concentrations. Culture medium suspensions containing 0 (vehicle-only), $0.5\times10^{-9}$ and $10^{-12}$ M concentration values were prepared for each nanomaterial and dead cell percentages were calculated for each case after 24 h of incubation. It was observed that the administration of all three types of nanomaterials induced an increase in the number of dead cells compared to the vehicle controls (Table 1). The data also indicate significant differences between the $0.5\times10^{-9}$ M suspensions and the $10^{12}$ M suspensions containing the same type of nanomaterial ($P<0.05$). Table 1 also illustrates differences related to type of nanomaterials at the same concentration values. The number of dead cells induced at a low concentration ($10^{-12}$ M) was highest in SW-CNTs (7.81±1.10%), followed, in descending order by Ag-NP (4.72±0.64%) and Au-NP (3.02±0.87%). Differences between various groups were found to be significant ($P<0.05$). Higher concentrations ($0.5\times10^{-9}$ M) of nanomaterials produced statistically significantly higher percentages of dead cells as compared to the lower concentrations of nanomaterials. The P-values were significant for both two concentrations (P<0.05).

TABLE 1

The percentage of MLOY4 dead cells when exposed to three different types of nanomaterials: nanoparticles of gold, nanoparticles of silver and single wall carbon nanotubes

| | Dead cell percentage (%) | | | |
|---|---|---|---|---|
| | Medium only (0.0 M) | Low concentration ($10^{-12}$ M) | High concentration ($0.5 \times 10^{-9}$ M) | P[a] |
| Au-NP | 2.63 ± 0.56 | 3.02 ± 0.87 | 4.10 ± 0.38 | <0.05 |
| Ag-NPs | 2.63 ± 0.56 | 4.72 ± 0.64 | 6.90 ± 0.89 | <0.05 |
| SW-CNTs | 2.63 ± 0.56 | 7.81 ± 1.10 | 11.58 ± 2.06 | <0.05 |

[a]P-values were calculated by means of one-way ANOVA test across the three concentration samples.

Individual and Combined Apoptotic Effect of Nanomaterials and Antiproliferative Agents Two established apoptotic agents, dexamethasone (D) and etoposide (E), were tested in combination with the different nanomaterials. Each nanomaterial at $0.5 \times 10^{-9}$ M concentration was separately delivered to the MLO-Y4 cell line in the presence as well as in the absence of D and E. Controls consisted of vehicle-only (ethanol+DMSO) cell cultures. The experimental results are presented in Table 2. Significantly higher numbers of dead cells were recorded for the nanomaterial-apoptotic combined samples as compared with nanomaterials only or D or E control samples (P<0.05 for all combined vs simple agent comparisons). Dead cell percent differences between etoposide and dexamethasone exposed samples were significant for all groups (P<0.05).

TABLE 2

Results of cells exposed to nanomaterials or nanomaterials in combination with the apoptotic agents (etoposide and dexamethasone)

| | Dead cell percentage (%) Nanomaterials | | | |
|---|---|---|---|---|
| Solutions | Control | Au-NPs added solution | Ag-NPs added solution | SW-CNTs added solution |
| Vehicle (ethanol + DMSO) | 2.25 ± 0.44 | 3.42 ± 0.41 | 6.58 ± 0.58 | 7.46 ± 0.73 |
| Dexamethasone (D + vehicle) | 4.47 ± 0.54 | 10.04 ± 1.10 | 12.85 ± 0.34 | 29.43 ± 0.78 |
| Etoposide (E + vehicle) | 7.64 ± 0.42 | 13.82 ± 0.70 | 19.60 ± 0.97 | 40.37 ± 0.81 |

As shown in Table 3, the apoptotic effect of both D and nanomaterial added groups were significantly greater than the simple additive effect exerted by dexamethasone and the nanomaterials alone (P<0.05 for each type of nanomaterial). The maximal increase for the synergistic effects in the presence of D was obtained for SW-CNTs (265.81%), followed by, Au-NPs (61.83%) and Ag-NPs (129.79%). The percentages of dead cells induced by the addition of nanomaterials and nanomaterials combined with etoposide and dexamethasone were calculated as follows: the real effect of the agents was done by subtracting the percentage of dead cells due to the vehicles alone from the percentage of dead cells after the administration of the agents (shown in column one). The second column shows the 'additive effects' or the expected effects calculated individually for each type of nanomaterials and etoposide and dexamethasone. The third column represents the measured combined effects of the nanomaterials combined with the apoptotic agents after the subtraction of the vehicle effect. The fourth column shows the percentage increase of the effects as measured experimentally, relative to the expected additive effects {[(real effect−additive effect)/additive effect]×100%}. Groups that were exposed to both E and each type of nanomaterial demonstrated similar increased response and cytotoxicity hierarchy. Increase of additive effect was found to be significantly higher in Etoposide administered samples (P<0.05 for each nanomaterial). FIG. 10 shows the induced cellular apoptotic effects due to the combination of silver nanoparticles and E.

TABLE 3

Individual and combined dead cell percentages due to the delivery of nanomaterials alone and nanomaterials along with dexamethasone or etoposide

| | | Additive effect[b] | | Combined effect[c] | | Increase of additive effect[d] | |
|---|---|---|---|---|---|---|---|
| Nanomaterial or agent effect[a] | | D-added samples | E-added samples | D-added samples | E-added samples | D-added samples | E-added samples |
| Au-NPs | 1.17 ± 0.44 | 3.39 ± 0.44 | 4.34 ± 0.42 | 7.79 ± 1.10 | 11.57 ± 0.70 | 129.79% | 166.58% |
| Ag-NPs | 4.33 ± 0.58 | 6.55 ± 0.54 | 7.50 ± 0.58 | 10.60 ± 0.34 | 17.35 ± 0.97 | 61.83% | 131.33% |
| SW-CNTs | 5.21 ± 0.73 | 7.43 ± 0.73 | 8.38 ± 0.42 | 27.18 ± 0.78 | 38.12 ± 0.81 | 265.81% | 354.89% |
| Dexamethasone | 2.22 ± 0.54 | | | | | | |
| Etoposide | 3.17 ± 0.42 | | | | | | |

Apoptotic Agents and Caspase-3 Activation Mechanism

Figure 11A:
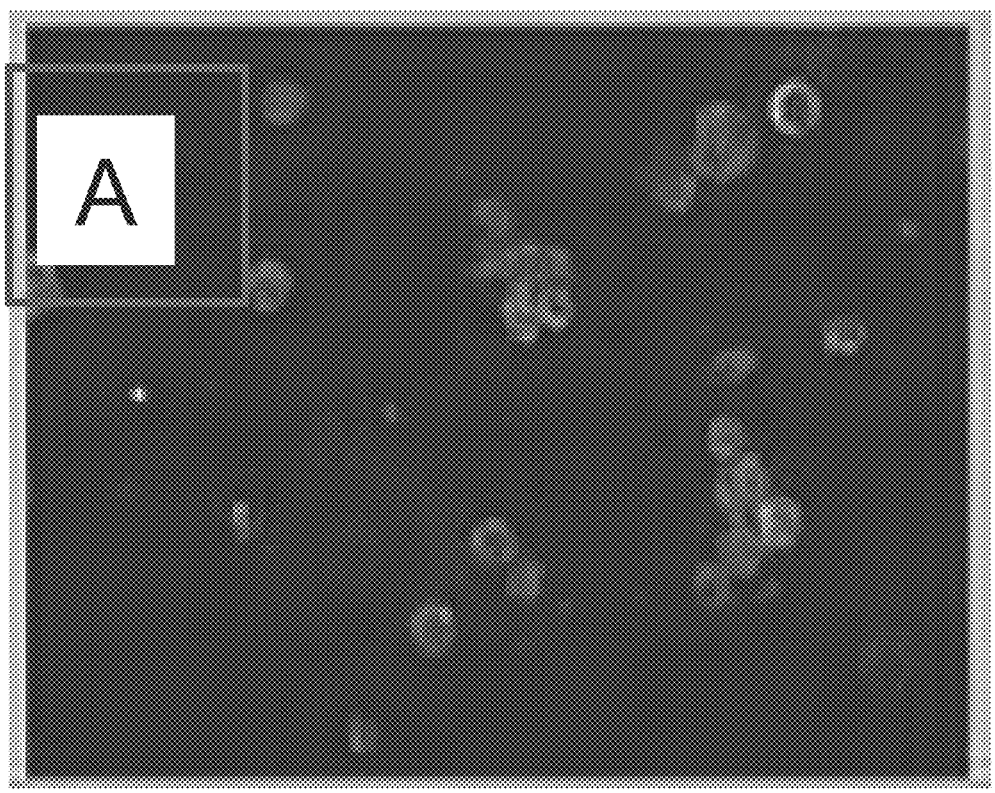
Figure 11B:
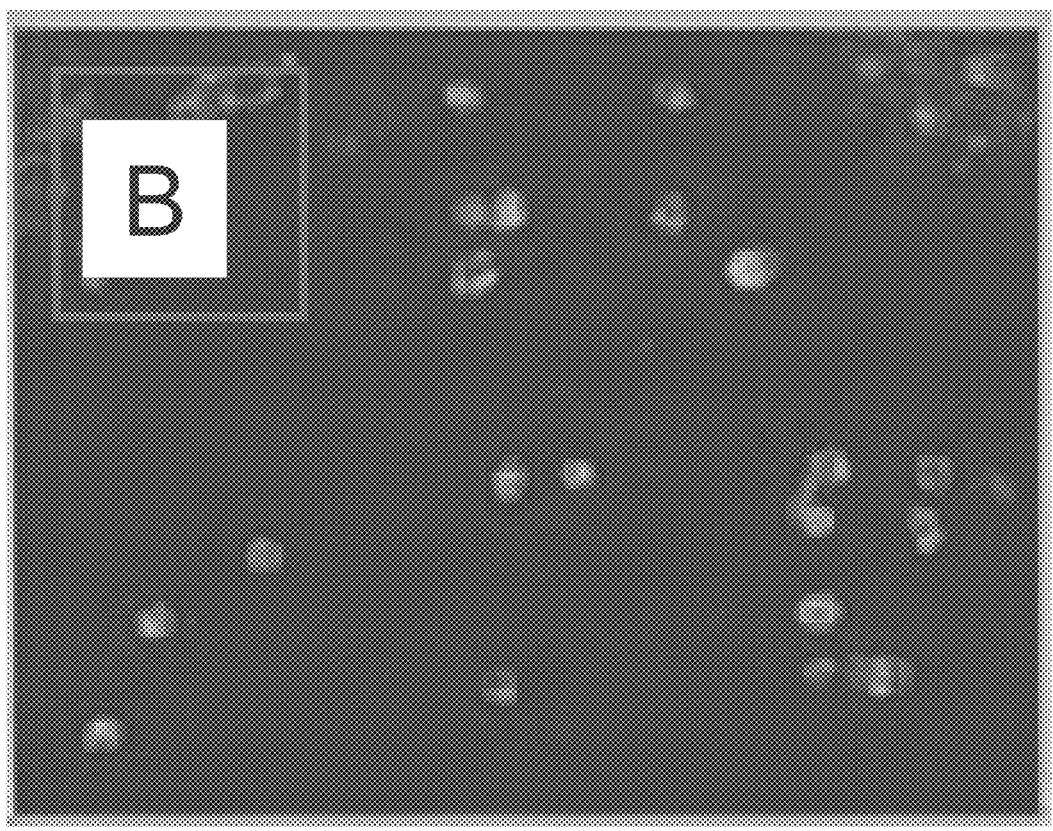
Figure 11C:
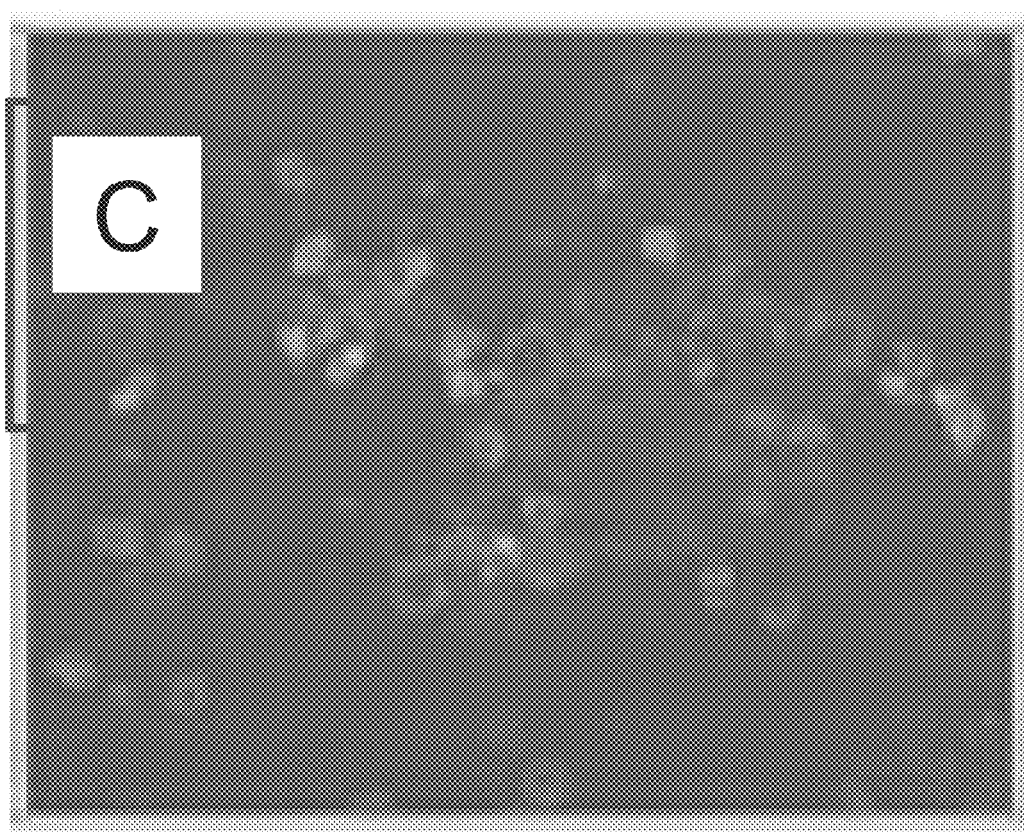
Figure 11D:
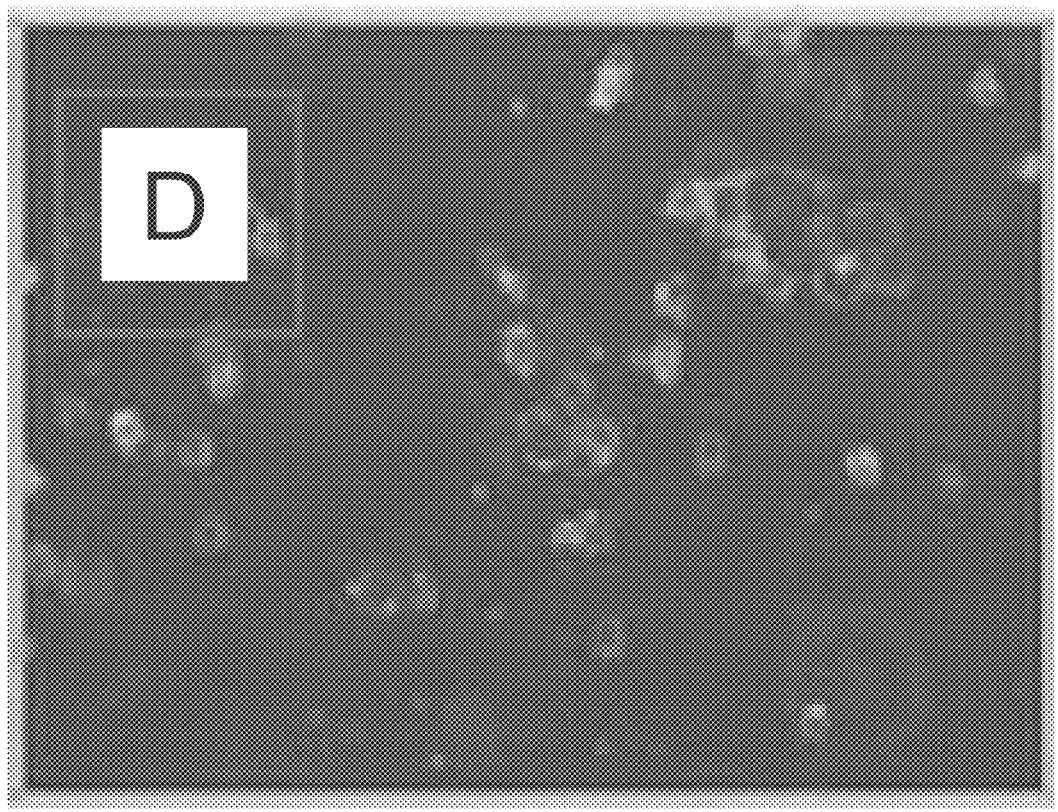
Figure 11E:
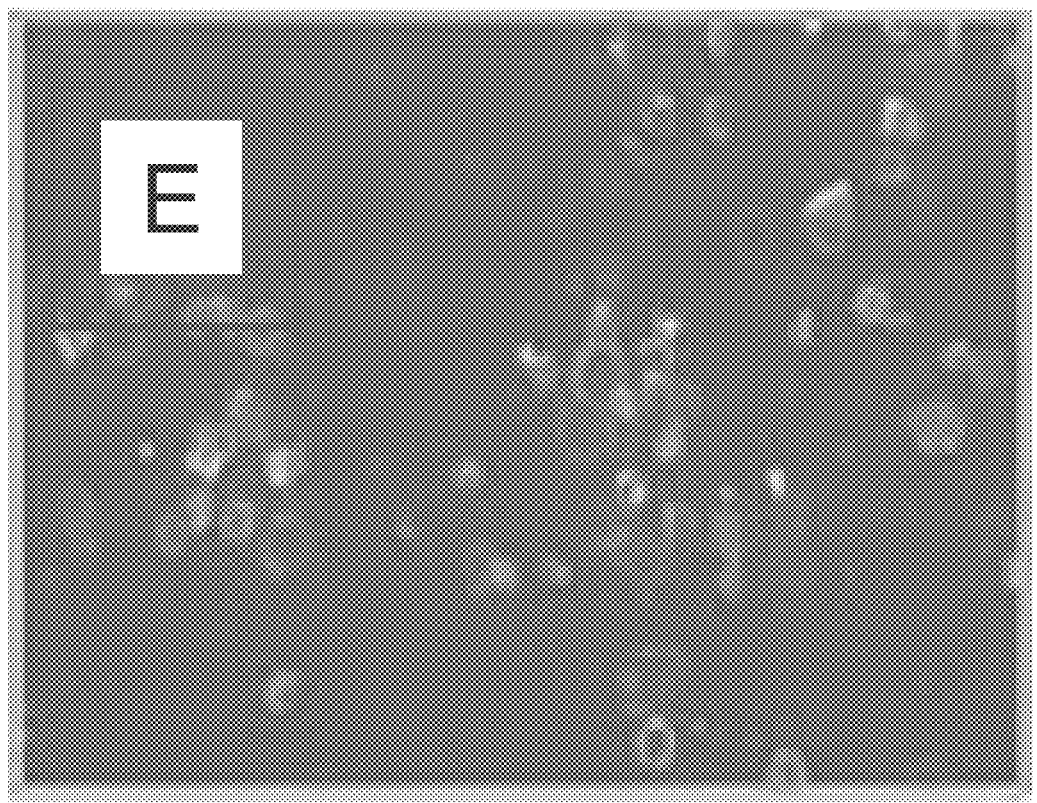
Figure 11F:
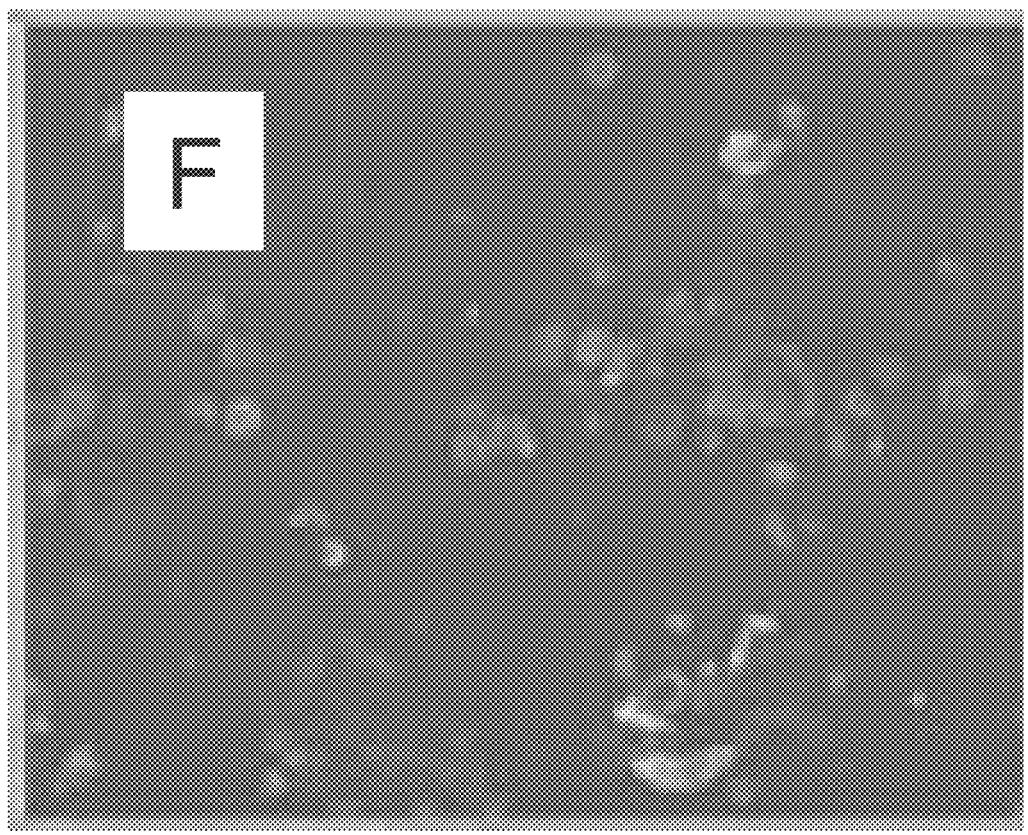
Figure 11G:
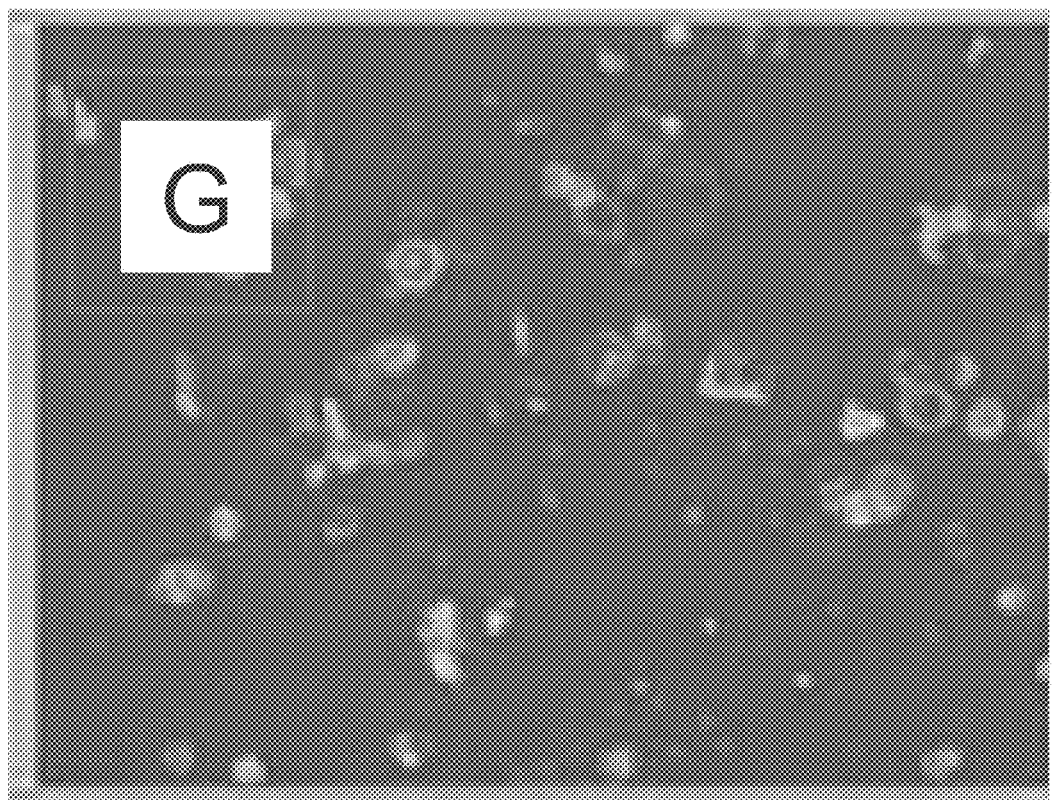
Figure 11H:
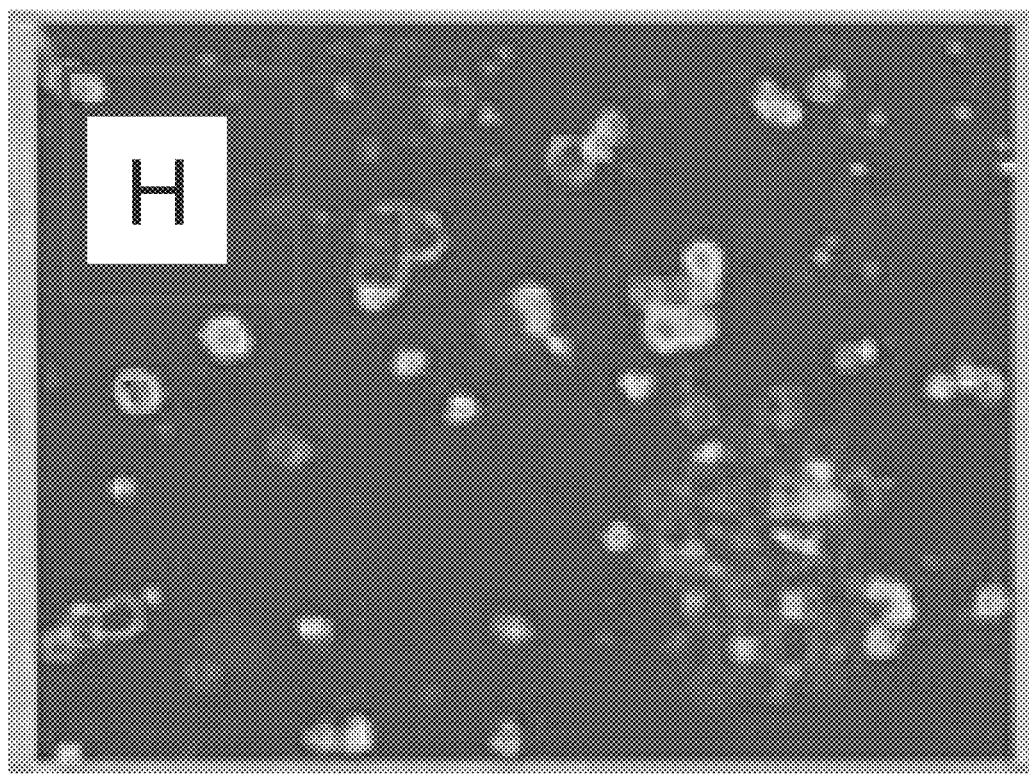
Figure 11I:
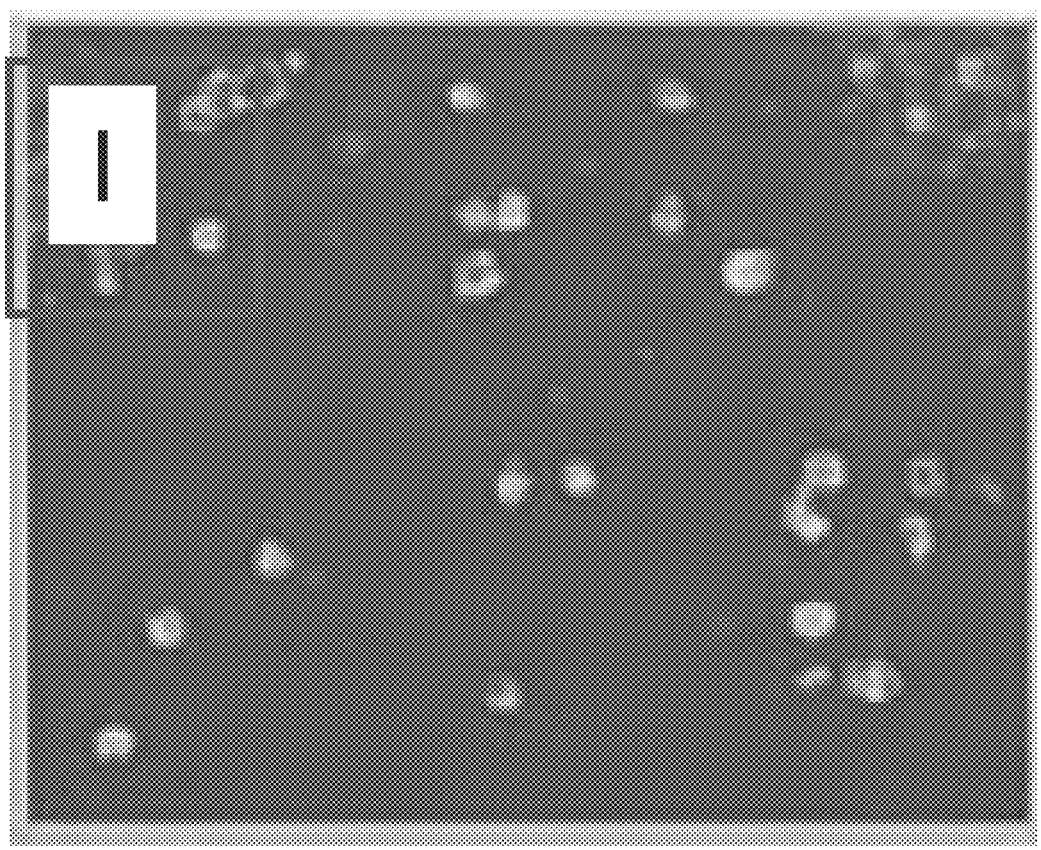
Figure 11J:
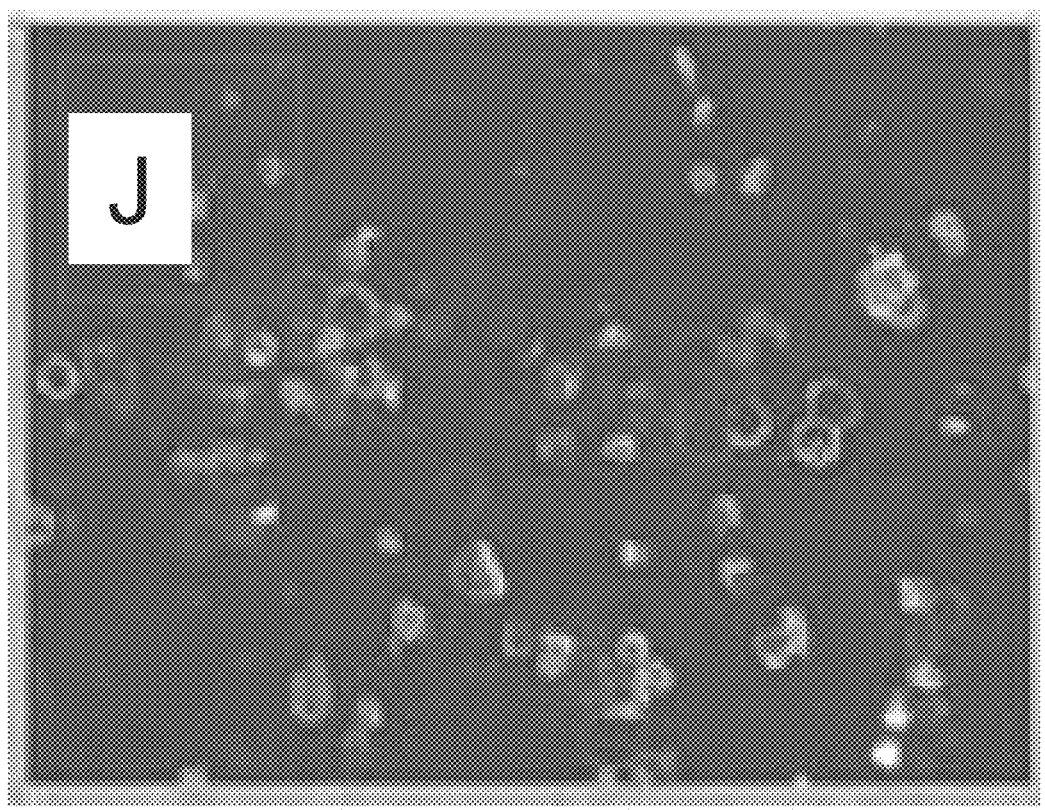
Figure 11K:
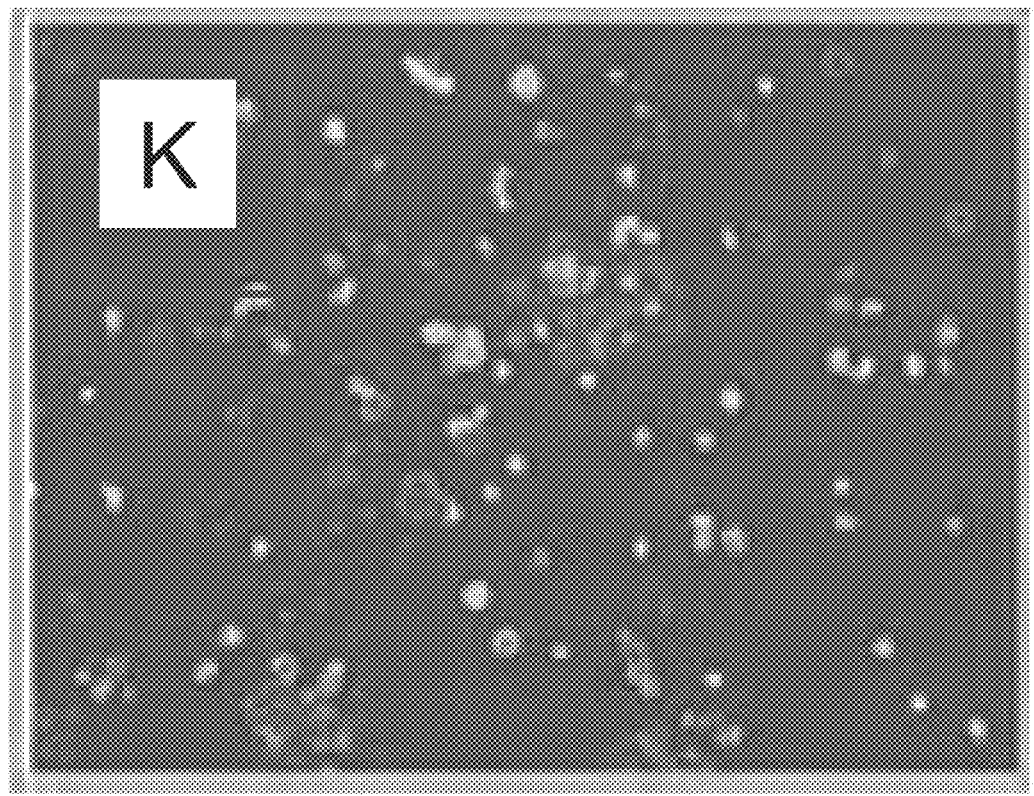

The use of the active form of caspase-3 for the detection of early apoptotic events was investigated. The cells were treated with different nanomaterials with and without the addition of apoptotic agents and labeled with a Red-DEVD-FMK Caspase 3 staining kit as described above. The results are presented in FIG. 11. Caspase-3 activation was evaluated by the intensity of the red stain in each sample using a fluorescent microscope. Brighter red stains show more cleaved caspase-3. FIGS. 11I, 11J and 11K contain a larger number of cells having the bright red staining compared with FIGS. 11A-11H. Combined apoptotic agents induced higher levels of staining than simple added samples. The combination of the SW-CNTs with the etoposide shows the most significant activation and the majority of the cells appear with bright red stain compared with the low brightness of the red stain with lower caspase-3 activation level and the non-apoptotic cells appear with a dark background that can be observed in the rest of the samples.

DISCUSSIONS

Nanoparticles may cause adverse effects because of their small size and unique properties, as already indicated by earlier studies [52]. The nanoparticles are believed to be highly mobile in the human body or various biological environments and appear to penetrate and accumulate in different tissues [46] or they are sequestered in various intracellular compartments or organelles. Although several studies indicated different mechanisms of nanoparticle sequestration, endocytosis is believed to be the most probable method of uptake [40, 51]. Once the nanoparticles penetrate into the cytoplasm or the nucleus, they are thought to strongly interact with various protein and nucleic acid structures within these compartments and could either enhance or limit various cellular functions. Endocytosis of nanomaterials can trigger the binding of nanoparticles to intracellular targets, which could cause alterations in cellular signaling, motility and metabolism. The experiments described above were aimed at evaluating the in vitro cellular response to three different types of nanoparticles (Au-NPs, Ag-NPs and SW-CNT).

It was initially observed that the nanomaterials became sequestered intracellularly within the first few hours of incubation. Since this was the time at which the first microscopic measurements were made, it is possible that incorporation into the cellular compartments occurred at an earlier time point. The effect of these nanomaterials on cellular morphology was then evaluated. The data suggest that uptake of the different types of nanomaterials resulted in cell shape alterations that were found to be dependent upon the type of nanomaterial, its concentration and physical properties.

These results demonstrate several aspects of nanomaterials cytotoxicity. The first experimental result suggests that the higher concentrations of nanoparticles induced a higher percentage of dead cells that were independent of the type of nanomaterial. These findings also reveal differences in the cellular apoptotic response that were a function of the combination of the various physical and chemical properties of the nanomaterial. For example, the tubular shape and the diameter of nanomaterials such as the carbon nanotubes compared with spherical Ag and Au nanoparticles could be reflected in a different uptake rate within the cells due their different physical interaction with the cellular membrane. Moreover the presence of various functional groups on the surface of the nanomaterials could highly impact their interaction with the cellular membranes and their penetration abilities inside the cells. Although further experiments are needed to clearly demonstrate the independent responses among all possible physical and chemical factors involved, our data clearly confirms some very recent reports. For example, like previously reported, we also obtained increased cytotoxicity when the cells were exposed to the smaller size nanomaterials [45]. Among the three nanomaterials evaluated, the carbon nanotubes have the smallest size (diameter 1.2 nm) and appeared to be the most cytotoxic. While not wishing to be bound by theory, the high level of apoptosis induced by carbon nanotubes could be a result of their tubular shape as well as their chemical composition. The lack of their shape similarity with most human body particles may generate non-self recognition mechanisms. Electrical surface charge as well as intrinsic chemical specificity can also constitute important determinants in the observed cytotoxicity and need to be further explored.

One important part of our experimental approach is the apoptotic evaluation in comparison and in addition to the well-known apoptotic agents, such as dexamethasone and etoposide. The above results also suggest that nanomaterials and apoptotic agents may be synergistic in their mechanism of induction of the apoptotic process. The apoptotic response of all combinations of the various nanomaterials and either D or E showed a significantly higher response than a simple additive effect of nanomaterials or D or E alone. The greater the initial apoptotic response to the drug is, the greater the interaction with the nanomaterial and the greater the increase in cytotoxicity. Our data show that etoposide coupled with any type of nanomaterial tested results in higher cytotoxic response amplification compared with dexamethasone-coupled with the nanomaterials tested. Also, although the cytotoxicity of Ag-NPs alone was greater than that of the Au-NPs, the latter induced a greater increase in the dead cell percentages when tested in combination with both E and D, suggesting either the existence of different cell targets for the two nanomaterials or the existence of some protection mechanisms involved in the interaction of Ag-NPs with the cells. While not wishing to be bound by theory, these results provide clear evidence of nanomaterial activation potential for the caspase-3 apoptotic pathway either alone or in combination with dexamethasone or etoposide. The protease is responsible for the initiation of the death cascade and is therefore an important marker of the cells entry point into the apoptotic-signaling pathway [48]. Caspase-3 (cysteinyl aspartate-specific proteases) is one of the cytoplasmic caspase enzymes, which plays an important role in signaling various cellular death processes. It is a central intrinsic apoptotic factor in many cells and mediates the cleavage of other downstream caspases. The activation of caspase-3 is also a marker for cellular damage resulting from exposure to a number of anticancer agents. Their involvement as an indicator and as a potential target for drug treatment makes them widely researched molecules. The protease plays an important role in the execution of the apoptosis program, which is primarily responsible for the cleavage of poly ADP ribose protease (PARP) during cell death, which leads to the'degradation and the fragmentation of chromosomal DNA and apoptosis of the cell. The integration of the apoptotic agents and the nanomaterials with the death domain present in the cellular plasma membrane could lead to the up-regulation of pro-apoptotic specific proteins such as Bax. These protein families translocate from the cytosol to the mitochondria, which is preceded by the release of cytochrome-c. Such a process is attributed to the induction of the mitochondrial permeability transition, which is responsible for DNA damage leading to the necrosis inducement of cells. The action of some cofactors in the cytoplasm like apoptotic protease activating factor-1 (Apaf-1, a cytosolic protein involved in cell death), ATP/dATP, as well as the presence of some enzymes like pro-caspase-9, leads to the formation of the apoptosome complex in the cytoplasm which activates the caspase-9 that is responsible for the activation of the caspase-3 protein. Caspase-3, one of 13 aspartate-specific cystein proteases, plays an important role in the execution of the apoptosis program and is primarily responsible for the cleavage of PARP (poly ADP ribose protease) during cell death which leads to the degradation and the fragmentation of the chromosomal DNA inside the nucleus and apoptosis inducement of the cells [35, 37, 38, 24, 53, 54].

In normal cells, caspase-3 exists as a procaspase in which the potential cleavage site is intact. Once cleaved through the activation of the apoptotic cascade, the peptide end of this active caspase represents a novel epitope, which is not present in normal cells. Therefore, the detection of this novel epitope should be a unique and sensitive indicator of early apoptotic stages. Our caspase-3 activation evaluation results confirm that the apoptotic caspase-3 pathway is highly activated in combined apoptotic agents with the most elevated level recorded for combined etoposide and SW-CNT exposure. Results confirm the above discussed advantage of exposure to both agents over singular exposure in initiating early apoptotic events.

The above results provide evidence of multivariate approaches in nano-toxicology, with the inclusion of various factors with possible implications in cell apoptosis. Second, these results provide evidence of caspase activation by various nanomaterials. Third, these results demonstrate the existence of a synergistic apoptotic response when cells are exposed to nano-sized and several classical apoptotic agents. The present results allow for the development of new cancer therapies and contribute to the understanding of the process that is responsible for anti-cancer drug chemoresistance in cancer cells.

One result of the recent development of applications that make use of the unique properties of nanomaterials could be the induction of adverse health events in humans. When MLOY4 osteocytic cells were exposed to a variety of nanomaterials including silver and gold nanoparticles and single-wall carbon nanotubes, morphological and functional changes in the cells were induced. The cells changed their size, shape and more interesting their biological functions. These three nanomaterials were found to be responsible for inducing apoptotic processes in the cell, with the carbon nanotubes being the most aggressive. Moreover, it was found that nanomaterials alone and in combination with classical antiproliferative agents such as dexamethasone and etoposide, induced apoptosis by activation of caspase-3 pathway and therefore have a potential for use in chemotherapy.

While the foregoing specification teaches the principles of the present invention, with examples provided for the purpose of illustration, it will be appreciated by one skilled in the art from reading this disclosure that various changes in form and detail can be made without departing from the true scope of the invention.

REFERENCES

[1] Z. Liu, K. Chen, C. Davis, S. Sherlock, Q. Cao, X. Chen, H. Dai, Cancer Res. 2008, 68, 6652.
[2] M. Prato, K. Kostarelos, A. Bianco, Acc. Chem. Res. 2008, 41, 60.
[3] S. Hampel, D. Kunze, D. Haase, K. Kräamer, M. Rauschenbach, M. Ritschel, A. Leonhardt, J. Thomas, S. Oswald, V. Hoffmann, B. Büchner, Nanomed, 2008, 3, 175.
[4] P. Arimondo, C. Boukarim, C. Bailly, D. Dauzonne, C. Monneret Anti-Cancer Drug Design, 2000, 15, 413.
[5] A. Paola, B. Chawki, B. Christian, D. Daniel, M. Claude, Anti-cancer drug design, 2000, 15, 413.
[6] J. S. Kim, G. P. Amorino, H. Pyo, Q. Cao, H. Choy, Radiother. Oncol. 2002, 62, 61.
[7] K. D. Bromberg, A. B. Burgin, and N. Osheroff., J. Biol. Chem., 2003, 278, 7406.
[8] B. A. Teicher, Clin Cancer Res, 2008, 14, 1610.
[9] E. Thomas E, P. Dumas, J. A. Ajani, Invest New Drugs. 1999, 16, 333.
[10] S. M. Herbert, M. J. Brames, L. H. Einhorn. Journal of Clinical Oncology, 2006, 24, 18618.
[11] N. Hijiya, A. Gajjar, Z. Zhang, J. T. Sandlund, R. C. Ribeiro, J. E. Rubnitz, S. Jeha, W. Liu, C. Cheng, S. C. Raimondi, F. G. Behm, G. K. Rivera, M. V. Relling, and C. H. Pui, Leukemia, 2004, 18, 1581.
[12] C. L. Perkins, F. Guofu, K. N. Caryn, K. N. Bhalla., Cancer Research, 2000, 60, 1645.
[13] C. Stefanellia, B. Tantinia, M. Fattoria, I. Stanic'a, C. Pignattia, C. Clob, C. Guarnieri, C. M. Caldarerra, C. A. Mackintoshc, A. E. Peggc, F. Flamignia, FEBS Letters 2002, 527, 223.
[14] D. J. Smart, H. D. Halicka, G. Schmuck, F. Traganos, Z. Darzynkiewicz, and G. M. Williams, Mutat Res. 2008, 641, 43.
[15] P. Koistinen, T. Siitonen, P. Mäntymaa, E. Savolainen, Leukemia Research, 2001, 25, 1099.
[16] A. S. Moosavi, A. Tehranian, N. Behtash, M. Modares Gilani and F. Ghaemmaghami, Acta Medica Iranica, 2006, 44, 7.
[17] G. Spitaleri, D. V. Matei, G. Curiglianol, S. Detti, F. Verweij, S. Zambito, E. Scardino, B. Rocco, F. Nole, L. Ariu, T. De Pas, F. de Braud, O. D. Cobelli, Annals of Oncology, 2009, doi:10.1093/annonc/mdn650.
[18] M. J. Boyer, P. Mitchell, D. Goldstein, M. J. Millward, I. N. Olver, S. J. Clarke, G. Richardson, I. Davis, Lung Cancer, 2001, 32, 89.
[19] T. Morisaki, M. Katano, Curr. Med. Chem. 2003, 10, 2517.
[20] J. Li, M. Srinivasula, L. Feng-Ting, A. C. Newland, T. Fernandes-Alnemri, E. S. Alnemri, S. M. Kelsey, Blood, 2001, 98, 414.
[21] H. Mirzaie-Joniani, D. Eriksson, A. Sheikholvaezin, A. Johansson, P. O. Löfroth, L. Johansson, T. Stigbrand, Cancer, 2002, 94, 1210.
[22] P. Seminara, C. Pastore, C. Iascone, F. Cicconetti, G. Nigita, T. Ielapi, F. Franchi, Chemotherapy, 2007, 53, 218.
[23] R. K. Reddy, C. Mao, P. Baumeister, R. C. Austin, R. J. Kaufman, A. S. Lee, Biol. Chem., 2003, 278, 20915.
[24] T. Panaretakis, K. Pokrovskaja, M. C. Shoshan, and D. Grandér, J. Biol. Chem., 2002, 277, 44317.
[25] L. T. Wen, C. C. Caldwell, and A. F. Knowles, Cells, 2003, 63, 706.
[26] J. M. Van Maanen, J. Retèl, J. de Vries, H. M. Pinedo, J Natl Cancer Inst., 1988, 80, 1526.
[27] J. H Hwang, J. Y. Kim, M. I. Cha, I. N. Ryoo, S. J. Choo, S. M. Cho, Y. Tsukomu, A. Tomida, K. Shin, Y. I. Hwang, I. D. Yoo, H. R. Park. J. Cell. Physiol., 2008, 215, 243.
[28] M. S. Soengas, P. Capodieci, D. Polsky, Nature, 2001, 409, 207.
[29] G. S. Wu, Z. Ding, Oncogene, 2002, 21, 1.
[30] T. L. Rothstein, Cell Research, 2000, 10, 245.

[31] S. K. Manna, S. Sarkar, J. Barr, K. Wise, E. V. Barrera, O. Jejelowo, A. C. Rice-Ficht, G. T. Ramesh, Nano Lett., 2005, 5, 1676.

[32] N. W. Shi Kam, T. C. Jessop, P. A. Wender, H. Dai, J Am Chem. Soc., 2004, 126, 6850.

[33] N. Andre, X. Tian, M. Lutz, L. Ning, Science, 2006, 311, 622.

[34] E. Shashkov, M. Everts, E. Galanzha, V. Zharov, Nano Lett., 2008, 8, 3953.

[35] Alnemri E S, Livingston D J, Nicholson D W, Salvesen G, Thornberry N A, Wong W W, Yuan J. 1996. Human ICE/CED-3 protease nomenclature. *Cell* 87: 171.

[36] Borm P J, Robbins D, Haubold S, Kuhlbusch T, Fissan H, Donaldson K, Schins R, Stone V, Kreyling W, Lademann J. 2006. The potential risk of nanomaterials: a review carried out for ECETOC. *Part. Fibre Toxicol.* 3:11-46.

[37] Boulares A H, Yakovlev A G, Ivanova V, Stoica B A, Wang G, Iyer S, Smulson M. 1999. Role of poly (ADP-ribose) polymerase (PARP) cleavage in apoptosis. *J. Biol. Chem.* 274: 22932-22940.

[38] Cryns V, Yuan J. 1998. Proteases to die for. *Genes Dev.* 12: 1551-1570.

[39] Dong W, Zhang T, Epstein J, Cooney L, Wang H, Li Y, Jiang Y, Cogbill A, Varadan V, Tian R Z. 2007. Multifunctional nanowire bioscaffolds on titanium. *Chem. Mater.* 19: 4454-4459.

[40] Geiser M, Rothen-Rutishauser B, Kapp N, Schurch S, Kreyling W, Schulz H, Semmler M, ImHof V, Heyder J, Gehr P. 2005. Ultrafine particles cross cellular membranes by nonphagocytic mechanisms in lungs and in cultured cells. *Environ. Health Perspect.* 113: 1555-1560.

[41] Harrison B S, Atala A. 2007. Carbon nanotube applications for tissue engineering. *Biomaterials* 28: 344-353.

[42] Hirsch L R, Stafford R J, Bankson J A, Sershen S R, Rivera B, Price R E, Hazle J D, Halas N J, West J L. 2003. Nanoshell-mediated near-infrared thermal therapy of tumors under magnetic resonance guidance. *Proc. Natl Acad. Sci. USA* 100: 13549-13554.

[43] Joe E K, Wei X, Anderson R R, Lin C P. 2003. Selective cell targeting with light-absorbing microparticles and nanoparticles. *Biophys. J.* 84: 4023-4032.

[44] Kam N W S, O'Connell M, Wisdom J A, Dai H. 2005. Carbon nanotubes as multifunctional biological transporters and near-infrared agents for selective cancer cell destruction. *Proc. Natl Acad. Sci.* 102: 11600-11605.

[45] Kang S, Herzberg M, Rodrigues D F, Elimelech M. 2008. Antibacterial effects of carbon nanotubes: size does matter! *Langmuir* 24: 6409-6413.

[46] Liu Z, Davis C, Cai W, He L, Chen X, Dai H.2008. Circulation and long-term fate of functionalized, biocompatible single-walled carbon nanotubes in mice probed by Raman spectroscopy. *Proc. Natl. Acad. Sci.* 105: 1410-1415.

[47] National Research Council. 2007. *Toxicity Testing in the 21st Century: a Vision and a Strategy*. National Academic Press: Washington, D.C.

[48] Nicholson D W, Ali A, Thornberry N A, Vaillancourt J P, Ding C K, Gallant M, Gareau Y, Griffin P R, Labelle M, Lazebnik Y A, Munday N A, Raju S M, Smulson M E, Yamin T T, Yu V L, Miller D K. 1995. Identification and inhibition of the ICE/CED-3 protease necessary for mammalian apoptosis. *Nature* 376: 37-43.

[49] Oberdorster G, Oberdorster E, Oberdorster J. 2005b. Nanotoxicology: An emerging discipline evolving from studies of ultrafine particles. *Environ. Health Perspect.* 133: 823-839.

[50] Panyam J, Labhasetwar V. 2003. Biodegradable nanoparticles for drug and gene delivery to cells and tissue. *Adv. Drug Del. Rev.* 55: 329-347.

[51] Rothen-Rutishauser B M, Schurch S, Haenni B, Kapp N, Gehr P. 2006. Interaction of fine particles and nanoparticles with red blood cells visualized with advanced microscopic techniques. *Environ. Sci. Technol.* 40:4353-4359.

[52] Sayes C M, Liang F, Hudson J L, Mendez J, Guo W, Beach J M, Moore V C, Doyle C D, West J L, Billups W E, Ausmanb K D, Colvin V L. 2006. Functionalization density dependence of single-walled carbon nanotubes cytotoxicity in vitro. *Toxicol. Lett.* 161: 135-142.

[53] Tewari M, Quan L T, O'Rourke K, Desnoyers S, Zeng Z, Beidler D R, Poirier G G, Salvesen G S, Dixit V M. 1995. Yama/CPP32 beta, a mammalian homolog of CED-3, is a CrmA-inhibitable protease that cleaves the death substrate poly(ADP-ribose) polymerase. *Cell* 81: 801-809.

[54] Wen L T, Caldwell C C, Knowles A F. 2003. Poly(ADP-ribose) polymerase activation and changes in Bax protein expression associated with extracellular ATP-mediated apoptosis in human embryonic kidney 293-P2X7 cells. *Mol. Pharmacol.* 63: 706-713.

[55] Xia T, Kovochich M, Brant J, Hotze M, Sempf J, Oberley T, Sioutas C, Yeh J I, Wiesner M R, Nel A E. 2006. Comparison of the abilities of ambient, and manufactured nanoparticles to induce cellular toxicity according to an oxidative stress paradigm. *Nanoletters* 6: 1794-1807.

[56] Zanello L P, Zhao B, Hu H, Haddon R C. 2006. Bone cell proliferation on carbon nanotubes. *Nanoletters* 6: 562-567.

[57] Zharov V, Galitovsky V, Viegas M. 2003. Photothermal detection of local thermal effects during selective nanophotothermolysis. *Appl. Phys. Lett.* 83: 4897-4899.

[58] Zharov V P, Galitovskaya E N, Jonson C, Kelly T. 2005. Synergistic enhancement of selective nanophotothermolysis with gold nanoclusters: potential for cancer therapy. *Laser Surg. Med.* 37: 219-226.

What is claimed is:

1. A composition comprising:
   nanoparticles selected from the group consisting of single wall carbon nanotubes, silver nanoparticles, gold nanoparticles and combinations thereof; and
   etoposide.

2. The composition of claim 1, further comprising quantum dots.

3. The composition of claim 1, wherein the nanoparticles are not surface modified.

4. The composition of claim 1, wherein the etoposide is not conjugated to the nanoparticles.

5. The composition of claim 1, wherein the etoposide is not covalently conjugated to the nanoparticles.

6. The composition of claim 1, further comprising a pharmaceutically acceptable carrier or excipient.

7. The composition of claim 1, wherein the nanoparticles are selected from the group consisting of silver nanoparticles, gold nanoparticles and combinations thereof.

8. The composition of claim 1, wherein the composition comprises gold nanoparticles.

9. The composition of claim 8, further comprising quantum dots.

10. The composition of claim 1, further comprising dexamethasone.

\* \* \* \* \*